US009446087B2

(12) United States Patent
Krempin et al.

(10) Patent No.: US 9,446,087 B2
(45) Date of Patent: Sep. 20, 2016

(54) ANTI-RESORPTIVE AND BONE BUILDING DIETARY SUPPLEMENTS AND METHODS OF USE

(76) Inventors: David W. Krempin, Temecula, CA (US); Laurie Krempin, legal representative, Temecula, CA (US); Mary A. Murray, Irvine, CA (US); Yumei Lin, Long Beach, CA (US); Kevin W. Gellenbeck, Poway, CA (US); Silvia R. da Costa, Redondo Beach, CA (US); Leon M. Wilkins, North Andover, MA (US); Haeri Roh-Schmidt, Stockton, CA (US); Jatinder Rana, Grand Rapids, MI (US); John F. Rebhun, Greenville, MI (US); David J. Fast, Grand Rapids, MI (US)

( * ) Notice: Subject to any disclaimer, the term of this patent is extended or adjusted under 35 U.S.C. 154(b) by 811 days.

(21) Appl. No.: 11/977,696

(22) Filed: Oct. 24, 2007

(65) Prior Publication Data

US 2008/0199545 A1  Aug. 21, 2008

Related U.S. Application Data

(60) Provisional application No. 60/854,312, filed on Oct. 24, 2006, provisional application No. 60/925,914, filed on Apr. 23, 2007.

(51) Int. Cl.

| A61K 36/87 | (2006.01) |
|---|---|
| A61K 36/489 | (2006.01) |
| A61K 31/352 | (2006.01) |
| A61K 36/185 | (2006.01) |
| A61K 36/258 | (2006.01) |
| A61K 36/484 | (2006.01) |
| A61K 36/804 | (2006.01) |

(52) U.S. Cl.
CPC ........... *A61K 36/489* (2013.01); *A61K 31/352* (2013.01); *A61K 36/185* (2013.01); *A61K 36/258* (2013.01); *A61K 36/484* (2013.01); *A61K 36/804* (2013.01); *A61K 36/87* (2013.01)

(58) Field of Classification Search
None
See application file for complete search history.

(56) References Cited

U.S. PATENT DOCUMENTS

| 5,478,579 | A | 12/1995 | Sawruk |
| 5,504,105 | A | 4/1996 | Chiesi et al. |
| 5,571,186 | A | 11/1996 | Prezmeczky et al. |
| 6,060,063 | A * | 5/2000 | Lansky .......................... 424/776 |
| 6,291,533 | B1 | 9/2001 | Fleischner |
| 6,579,543 | B1 * | 6/2003 | McClung ...................... 424/728 |
| 7,381,429 | B2 | 6/2008 | Erdelmeier et al. |
| 7,825,157 | B2 | 11/2010 | Ptchelintsev |
| 7,838,050 | B2 | 11/2010 | Randolph et al. |
| 2002/0009506 | A1 | 1/2002 | Tao |
| 2003/0008048 | A1 * | 1/2003 | Winston et al. .............. 426/548 |
| 2004/0059110 | A1 | 3/2004 | Nakano et al. |
| 2004/0151788 | A1 | 8/2004 | Gluck et al. |
| 2004/0162247 | A1 | 8/2004 | Kim et al. |
| 2005/0032882 | A1 | 2/2005 | Chen |
| 2005/0079232 | A1 | 4/2005 | Offord-Cavin et al. |
| 2005/0143366 | A1 | 6/2005 | Pierce, Jr. et al. |
| 2005/0176654 | A1 | 8/2005 | Takagaki et al. |
| 2005/0181069 | A1 * | 8/2005 | McCleary .................... 424/686 |
| 2005/0181083 | A1 * | 8/2005 | Takagaki et al. ............. 424/770 |
| 2005/0202103 | A1 | 9/2005 | Rajendran et al. |
| 2005/0227910 | A1 | 10/2005 | Yang et al. |
| 2005/0232901 | A1 | 10/2005 | Zaghmout |
| 2006/0051316 | A1 | 3/2006 | Ohnogi et al. |

FOREIGN PATENT DOCUMENTS

| CN | 1105271 A | 7/1995 |
| CN | 1446549 | 10/2003 |
| CN | 2004/1026030 | 4/2004 |
| CN | 1490321 A | 4/2004 |
| CN | 1607932 A | 4/2005 |
| JP | 1999/0049884 | 2/1999 |
| JP | 2000247896 | 9/2000 |
| JP | 2002179585 A | 6/2002 |
| JP | 2004501201 | 1/2004 |
| JP | 2004175680 A * | 6/2004 |
| JP | 2006/117550 | 5/2006 |

(Continued)

OTHER PUBLICATIONS

Agnusdei et al., Efficacy of ipriflavone in established osteoporosis and long term safety, 1997, Calcif Tissue Int, 61: S23-7.*
Chen, et al., "Green Tea Catechin Enhances Osteogenesis in a Bone Marrow Mesenchymal Stem Cell Line", Osteoporos Int. 16:2039-45 (2005).
Ostrowska, et al., "Extra-Virgin and Refined Olive Oils Decrease Plasma Triglyceride, Moderately Affect Lipoprotein Oxidation Susceptibility and Increase Bone Density in Growing Pigs", J Sci. Food Agric. 86:1955-63 (2006).

(Continued)

*Primary Examiner* — Terry A. McKelvey
*Assistant Examiner* — Catheryne Chen
(74) *Attorney, Agent, or Firm* — Brinks Gilson & Lione; G. Peter Nichols

(57) ABSTRACT

Disclosed herein are dietary supplement compositions and methods for increasing or stimulating bone growth, decreasing or preventing bone resorption, increasing bone strength, improving bone structure, and improving bone architecture comprising a first composition comprising a combination of at least two of: quercetin, *Rehmannia* sp., *Rehmannia* sp. root, Siberian ginseng, *Sophora japonica*, licorice, and ipriflavone, wherein the combination of the first composition increases bone morphogenic protein-2 gene, promoter or protein expression; and a second composition comprising an extract of pomegranate in combination with at least one of Siberian ginseng, *Ginkgo biloba*, green tea, *Sophora japonica, Rehmannia* sp., grape seed, Dong Quai, and ipriflavone, wherein the combination of the second composition inhibits the expression of RANK-L.

10 Claims, No Drawings

(56) References Cited

FOREIGN PATENT DOCUMENTS

| KR | 2003/0033393 | | 5/2003 |
|---|---|---|---|
| KR | 2003/0057273 | | 8/2003 |
| WO | WO 92/13538 | * | 8/1992 |
| WO | WO 01/32191 A2 | | 5/2001 |
| WO | WO 01/87315 A1 | | 11/2001 |
| WO | WO 02/17909 A1 | | 3/2002 |
| WO | WO 03/057141 A2 | | 7/2003 |
| WO | WO 2004/091591 A2 | | 10/2004 |
| WO | WO 2005/025586 | | 3/2005 |
| WO | WO 2005/077396 A1 | | 8/2005 |
| WO | WO 2006/079243 A1 | | 8/2006 |

OTHER PUBLICATIONS

Puel, et al. "Dose-Response Study of Effect of Oleuropein, an Olive Oil Polyphenol, in an Ovariectomy/Inflammation Experimental Model of Bone Loss in the Rat", Clinical Nutrition 25:859-68 (2006).

Wattel, et al., "Flavonoid Quercetin Decreases Osteoclastic Differentiation Induced by RANKL Via a Mechanism Involving NFkB and AP-1", J Cell Biochem. 92:285-95 (2004).

Zhou, et al., "Estrogens Activate Bone Morphogenetic Protein-2 Gene Transcription in Mouse Mesenchymal Stem Cells", Mol. Endocrinol., 17(1):56-66 (Jan. 2003).

Tian, et al., "Effect of Soybean Isoflavone on Expression of Bone BMP2 and TGF—.beta.1 in Ovariectomized Rats", Zhongguo Gonggong Weisheng Zazhishe (2004), 20(9), 1079-1080 (2005). (Abstract).

Chen, et al., "Effects of Celosia Cristata L Flavonoid on Expression of Bone Morphogenetic Protein and Function of Tubular reabsorption of Rats with Diabetes Mellitus", Zhongguo Linchuang Kangfu (2005), 9(39), 188-190. (Abstract).

Yahara, et al., "Mechanical Assessment of Effects of Grape Seed Proanthocyanidins Extract of Tibial Bone Diaphysis in Rats", J Musculoskeletal Neuronal Interactions, (2):162-169 (2005). (Abstract).

Makoto, et al., Grape Seed Proanthocyanidins Extract Promotes Bone Formation in Rat's Mandibular Condyle, European J. Oral Sci, (113):47-52 (2005). (Abstract).

Puel, C., et al., Olive Oil and its Main Phenolic Micronutrient (oleuropein) Prevent Inflammation-Induced Bone Loss in the Ovariectomised Rat, Br. J. Nutrition, (94):119-127 (2004). (Abstract).

Patent Cooperation Treaty Search Report for PCT/US2007/022593.

Third Party Observation dated Apr. 7, 2010 (EPO Docket Date: Apr. 16, 2010) re EP Publication No. 2081570.

Bogar700 by Bogar, Ed. Ramachandran, Pub: Thamarai Noolagam Chennai (1994) p. 86, Formulation I.D. PD03/114; Formulation Name: Megathy Kuligai.

Athmarakshaamirtham by Kandasamy Mudaliar, Pub: Ilakkana Achagam, Chennai (1879) p. 574, Formulation I.D. AM05/2268, Formulation Name: Appiraka chendooram-3.

Rasatantrasarah Evam Siddhaprayogasamgrahah by Krishan Gopal Ayurveda Bhawan; Edn. 8$^{th}$, 1990 [This book contains back references from 1000 B.C. to 20$^{th}$ Century], pp. 367-368; Formulation ID: RS22/631; Formulation Name: Madhumalini Vasant.

European Search Report from Application No. 07 852 950.0 dated May 21, 2010.

Kropotov et al., "Effects of Siberian Ginseng Extract and Ipriflavone on the Development of Glucocorticoid-Induced Osteoporosis", Pharmacology and Toxicology, vol. 133(2), pp. 252-254, Mar. 2002.

Kropotov, A.V., et al., "Effects of Siberian Ginseng Extract and Ipriflavone of the Development of Glucocorticoid-Induced Osteoporosis", Bulletin of Experimental Biology and Medicine, vol. 133, No. 3, pp. 252-254 (Aug. 2002).

* cited by examiner

ANTI-RESORPTIVE AND BONE BUILDING DIETARY SUPPLEMENTS AND METHODS OF USE

This application claims priority to U.S. Provisional Application Ser. No. 60/854,312, filed Oct. 24, 2006 and U.S. Provisional Application Ser. No. 60/925,914, filed Apr. 23, 2007, the entire contents of which are hereby incorporated by reference.

BACKGROUND

Healthy bones continuously undergo a remodeling process, where an equilibrium is reached between bone resorption and bone formation through the concerted action of active bone cells, i.e. bone forming osteoblasts and bone resorbing osteoclasts. The bone remodeling process begins with activation of cells covering unmineralized bone, i.e. lining cells. The lining cells resorb the unmineralized bone, then retract and leave room for the osteoclasts which resorb the old, mineralized bone and create an environment which attracts the osteoblast to the same site. The osteoblasts thereafter lay down an organic matrix, which subsequently becomes mineralized to form new bone. Thus bone mass is determined by the balance between bone resorption by osteoclasts and bone formation by osteoblasts.

The amount of mineral in bone is largely responsible for its hardness, while substances like the structural protein collagen also contribute to bone's mechanical strength. The dense outermost bone is known as cortical bone while the more spongy internal form is known as cancellous or trabecular bone.

Most bone diseases are due to a disruption in the equilibrium of the bone remodeling process. Generally, the disruption is an increase in bone resorption. For example, osteoporosis, one of the most common bone diseases, is characterized by a decrease in bone mass along with a microstructural change in bone, but there is no effect on the chemical composition of bone itself which results in increased susceptibility to bone fractures. Specifically, the cortical bone becomes thin and porous while the trabecular bone becomes thinned, perforated, and disconnected. Osteoporosis may be considered the result of a negative balance in the bone remodeling cycle, i.e. less bone is formed than is being resorbed.

Thus, therapeutic agents for treating bone disorders are directed at inhibiting bone resorption and increasing bone formation. There are many different molecules and pathways involved in the bone remodeling process and the various therapeutic agents presently available target different molecules and pathways. For example, bisphosphonates (such as aledronate and risedronate) inhibit bone resorption by blocking osteoclast activity. Other therapeutic agents seek to inhibit bone resorption by blocking binding to members of the TNF receptor/ligand family, such as Receptor Activator for Nuclear Factor κB Ligand (RANK-L), a cytokine that activates osteoclasts, the cells that are involved in bone resorption. Inhibition of release of RANK-L prevents bone mineral loss.

Still other therapeutic agents target increasing bone formation. For example, activated bone morphogenic protein gene is known to have direct effects on triggering osteoblast cell differentiation and promoting bone formation. Delivery of recombinant bone morphogenic protein-2 (BMP-2) has been shown to induce bone or cartilage formation. However, systemic administration of pharmaceutical and biological agents, such as recombinant BMP-2, can have deleterious effects on the intestine and other tissues. Therefore, there is a need in the art for natural and plant-derived extracts, that can be used in dietary supplement interventions for preventing and/or treating bone disorders by inhibiting bone resorption and/or increasing bone formation.

BRIEF SUMMARY

The present invention is based on the discovery that novel combinations of various natural and plant-derived extracts can (1) inhibit bone resorption by inhibiting, decreasing, or preventing the expression and/or release of RANK-L, and/or by preventing calcium release from bones; (2) increase bone growth by increasing or stimulating gene and/or protein expression of BMP-2 and (3) improve or maintain bone strength.

In one example, the invention is a composition for increasing or stimulating bone growth comprising natural, plant-derived extracts, including a combination of at least two of the following: quercetin dihydrate, quercetin anhydrate, extract of *Rehmannia* sp., extract of *Rehmannia* sp. root, extract of Siberian ginseng, extract of *Sophora fructus japonica*, extract of *Sophora japonica*, extract of licorice, and ipriflavone, wherein the combination increases BMP-2 gene or protein expression.

In another example, the invention is a composition for increasing or stimulating bone growth comprising a combination of quercetin anhydrate or dihydrate, an extract of Siberian ginseng, an extract of *Sophora japonica*, and an extract of licorice, wherein the combination increases BMP-2 gene or protein expression.

In another example, the invention is a composition for increasing or stimulating bone growth comprising a combination of approximately 10-1000 mg of quercetin anhydrate or dihydrate, approximately 100-800 mg of an extract of Siberian ginseng, and approximately 10-500 mg of an extract of licorice, wherein the combination increases BMP-2 gene or protein expression.

In a further example, the invention is a composition for increasing or stimulating bone growth comprising a combination of approximately 10-1000 mg of quercetin anhydrate or dihydrate, and approximately 10-500 mg of an extract of licorice, wherein the combination increases BMP-2 gene or protein expression.

In another example, the invention is a composition for increasing or stimulating bone growth comprising a combination of approximately 10-1000 mg of quercetin anhydrate or dihydrate, and approximately 100-800 mg of an extract of Siberian ginseng, wherein the combination increases BMP-2 gene or protein expression.

In a further example, the invention is a method of increasing or stimulating bone growth in a subject, comprising administering to the subject a composition comprising a combination of at least two of the following: quercetin anhydrate, quercetin dihydrate, extract of *Rehmannia* sp., extract of *Rehmannia* sp. root, extract of Siberian ginseng, extract of *Sophora japonica*, extract of licorice, and ipriflavone, wherein the combination increases BMP-2 gene or protein expression in the subject.

A further example of the invention is a method of increasing or stimulating bone growth in a subject, comprising administering to the subject a composition comprising a combination of approximately 10-1000 mg of quercetin anhydrate or dihydrate, approximately 100-800 mg of an extract of Siberian ginseng, and approximately 10-500 mg of an extract of licorice, wherein the combination increases BMP-2 gene or protein expression in the subject.

Another example of the invention is a method of increasing or stimulating bone growth in a subject, comprising administering to the subject a composition comprising a combination of approximately 10-1000 mg quercetin anhydrate or dihydrate, and approximately 10-500 mg of an extract of licorice, wherein the combination increases BMP-2 gene or protein expression in the subject.

A further example of the invention is a method of increasing or stimulating bone growth in a subject, comprising administering to the subject a composition comprising a combination of approximately 10-1000 mg quercetin anhydrate or dihydrate, and approximately 100-800 mg of an extract of Siberian ginseng, wherein the combination increases BMP-2 gene or protein in the subject.

In another example, the present invention may be a composition for inhibiting, decreasing, or preventing bone resorption comprising a pomegranate extract, punicalagins, or both, in combination with one or more of the following: quercetin dihydrate, quercetin anhydrate, extract of *Rehmannia* sp., extract of *Rehmannia* sp. root, extract of Siberian ginseng, extract of *Sophora fructus japonica*, extract of *Sophora japonica*, extract of licorice, and ipriflavone, wherein the pomegranate extract, the punicalagins, or both inhibit expression, production, and/or release of RANK-L.

In one example, compositions and methods of the present invention utilize extracts of pomegranate (*Punica granatum*) fruit and peel which contain compounds known as punicalagins, to inhibit or decrease bone resorption. The extracts of pomegranate useful in the present invention, for example a pomegranate extract comprised of punicalagins, can be used in compositions and methods for inhibiting, decreasing, or preventing bone resorption, wherein the pomegranate extract inhibits, decrease or prevent the expression, production, and/or release of RANK-L. Accordingly, in one example the present invention is a composition for inhibiting, decreasing, or preventing bone resorption that comprises a pomegranate extract, at least one punicalagin, or both. Alternatively, the present invention contemplates a method of inhibiting, decreasing, or preventing bone resorption comprising administering a composition comprising a pomegranate extract, at least one punicalagin, or both, wherein the composition inhibits one of expression, production, and/or release of RANK-L.

In yet another example, the present invention is a composition for inhibiting, decreasing, or preventing bone resorption comprising natural, plant-derived extracts, including a combination of at least two of the following: an extract of pomegranate preferably containing punicalagins, an olive extract, an extract of Siberian ginseng, an extract of *Ginkgo biloba*, an extract of green tea, an extract of *Sophora japonica*, an extract of *Rehmannia* sp., an extract of grape seed, an extract of Dong Quai, and ipriflavone, wherein the combination inhibits expression, production, and/or release of RANK-L.

In a further example, the present invention is a composition for inhibiting, decreasing, or preventing bone resorption comprising a combination of an extract of pomegranate, an extract of grape seed, ipriflavone, and an extract of green tea, wherein the combination inhibits expression, production, and/or release of RANK-L.

In another example, the present invention is a composition for inhibiting, decreasing, or preventing bone resorption comprising a combination of approximately 10-2000 mg of an extract of pomegranate, approximately 35-250 mg of an extract of grape seed, and approximately 400-700 mg of ipriflavone, wherein the combination inhibits expression, production, and/or release of RANK-L.

In yet another example, the present invention is a composition for inhibiting, decreasing, or preventing bone resorption comprising approximately 10-2000 mg of an extract of pomegranate, approximately 35-250 mg of an extract grape seed, and approximately 400-700 mg of ipriflavone, wherein the composition inhibits release of calcium from bones.

Another example is a method of inhibiting, decreasing, or preventing bone resorption in a subject comprising administering to the subject a composition comprising natural, plant-derived extracts, including a combination of at least two of the following extracts: an extract of pomegranate, an olive extract, an extract of Siberian ginseng, an extract of *Ginkgo biloba*, an extract of green tea, an extract of *Sophora japonica*, an extract of *Rehmannia* sp., an extract of grape seed, an extract of Dong Quai, and ipriflavone, wherein the combination inhibits expression, production, and/or release of RANK-L.

In a further example, the invention is a method of inhibiting, decreasing, or preventing bone resorption in a subject comprising administering to the subject a composition comprising a combination of an extract of pomegranate, an extract of grape seed, ipriflavone, and an extract of green tea, wherein the combination inhibits expression, production, and/or release of RANK-L.

In a further example, the invention is a method of inhibiting, decreasing, or preventing bone resorption in a subject comprising administering to the subject a composition comprising a combination of approximately 10-2000 mg of an extract of pomegranate, approximately 35-250 mg of an extract of grape seed, and approximately 400-700 mg of ipriflavone, wherein the combination inhibits expression, production, and/or release of RANK-L.

In yet another example, the invention is a method of inhibiting, decreasing, or preventing bone resorption in a subject comprising administering to the subject a composition comprising a combination of approximately 10-2000 mg of an extract of pomegranate, approximately 35-250 mg of an extract of grape seed, and approximately 400-700 mg of ipriflavone, wherein the combination inhibits release of calcium from bones.

In a further example, the invention is a dietary supplement regimen for increasing or stimulating bone growth and inhibiting, decreasing, or preventing bone resorption comprising a first composition comprising a combination of at least two of quercetin dihydrate, quercetin anhydrate, an extract of *Rehmannia* sp., an extract of *Rehmannia* sp. root, an extract of Siberian ginseng, an extract of *Sophora japonica*, an extract of licorice, and ipriflavone, wherein the combination of the first composition increases the expression and/or activity of BMP-2; and a second composition comprising a combination of at least two of an extract of pomegranate, an olive extract, an extract of Siberian ginseng, an extract of *Ginkgo biloba*, an extract of green tea, an extract of *Sophora japonica*, an extract of *Rehmannia* sp., an extract of grape seed, an extract of Dong Quai, and ipriflavone, wherein the combination of the second composition inhibits the expression of RANK-L.

DETAILED DESCRIPTION

It is to be understood that this invention is not limited to the particular compositions, methodology, or protocols described herein. Further, unless defined otherwise, all technical and scientific terms used herein have the same meaning as commonly understood to one of ordinary skill in the art to which this invention belongs. It is also to be understood that the terminology used herein is for the purpose of describing particular embodiments only, and is not intended to limit the scope of the present invention, which will be limited only by the claims.

The present invention is based on the surprising discovery that unique combinations of ingredients including two or more of the following: quercetin anhydrate, quercetin dihydrate, extract of *Rehmannia* sp., extract of *Rehmannia* sp. root, extract of Siberian ginseng, extract of *Sophora japonica*, extract of licorice, extract of ipriflavone, extract of pomegranate, extract of olive, extract of *Ginkgo biloba*, extract of green tea, extract of grape seed, and extract of Dong Quai, which are described more fully below, increase bone growth by increasing or stimulating expression and/or activity of the BMP-2 promoter, gene, and or/protein, or inhibit bone resorption by either inhibiting, decreasing, or preventing RANK-L expression, production, or release or by inhibiting, decreasing, or preventing release of calcium from bones.

BMP-2 is a member of a family of bone morphogenic proteins, which are novel factors in the extended transforming growth factor B superfamily. Recombinant BMP-2 and BMP-4 can induce new bone formation when injected locally into the subcutaneous tissues of rats (Wozney J. Molec (1992) 32: 160-67). BMP-2 and BMP-4 are expressed by normal osteoblasts as they differentiate, and have been shown to stimulate osteoblast differentiation and bone nodule formation in vitro as well as bone formation in vivo. Thus, by increasing or stimulating BMP-2 promoter activity, gene expression, and/or protein expression, the unique compositions of the present invention are useful for increasing or stimulating bone growth and treating or preventing a variety of bone disorders.

RANK-L, receptor activator of nuclear factor (NF)-kB ligand (also: Osteoprotegerin ligand, OPGL) a member of the Tumor Necrosis Factor (TNF) family, is the main stimulatory factor for the formation of mature osteoclasts, bone cells that aid in bone resorption, and is essential for their survival. RANK-L is produced by osteoblastic lineage cells and activated T lymphocytes. It activates the specific receptor RANK that is located on osteoclasts and dendritic cells. One strategy for a formulation of the present invention is to directly inhibit RANK-L expression when stimulated by IL-1. Activation of RANK-L when stimulated with IL-1 can directly trigger osteoclastogenesis (and thus bone resorption). Thus, by inhibiting, decreasing, or preventing RANK-L expression, production, or release, the unique compositions of the present invention are useful for inhibiting, decreasing, or preventing bone resorption and treating or preventing a variety of bone disorders including bone loss, osteoporosis, osteolytic bones, etc.

Quercetin, which refers to quercetin extract(s) and the various forms of quercetin, such as quercetin dihydrate, quercetin anhydrate, etc., is one compound that is useful in unique compositions of the present invention. Quercetin is a flavonoid that forms the "backbone" for many other flavonoids, including the citrus flavonoids rutin, hesperidin, naringin and tangeritin. Quercetin is found to be the most active of the flavonoids in studies, and many medicinal plants owe much of their activity to their high quercetin content. Quercetin has demonstrated significant anti-inflammatory activity because of direct inhibition of several initial processes of inflammation. For example, it inhibits both the manufacture and release of histamine and other allergic/inflammatory mediators. In addition, it exerts potent antioxidant activity and vitamin C-sparing action.

Quercetin also may have positive effects in combating or helping to prevent cancer, prostatitis, heart disease, cataracts, allergies, inflammations, and respiratory diseases such as bronchitis and asthma. In addition, according to U.S. Pat. No. 5,478,579, when used in amounts ranging from 50-1500 mg/day, quercetin anhydrate and/or quercetin dihydrate can enhance absorption of calcium into bone tissues.

Foods rich in quercetin include apples, black & green tea, onions, raspberries, red wine, red grapes, citrus fruits, broccoli, fava beans, other leafy green vegetables, and cherries.

As discussed more fully below, the present invention is based in part on the discovery that quercetin is a potent activator of BMP-2 promoter activity and protein expression. In addition, the assay results discussed below demonstrate that when quercetin dihydrate is administered in combination with Siberian ginseng, licorice, or both, the combination achieves a surprising synergy resulting in BMP-2 promoter activity and protein expression beyond that achieved with any ingredient alone.

A quercetin ingredient used in the present invention may be obtained commercially from various sources including, for example, Twinlab (American Fork, Utah), Jarrow Formulas (Los Angeles, Calif.), Natural Factors (Coquitlam, British Columbia, Canada), and NOW Foods (Bloomingdale, Ill.). In addition, quercetin may be obtained by any of the extraction methods discussed more fully below, or described or known in the art.

*Rehmannia*, another plant useful in unique compositions of the present invention, is a genus of six species of flowering plants in the order Lamiales, endemic to China. Known as dihuang (地黄) in Chinese, this medicinal herb is used for a variety of ailments such as anemia, dizziness and constipation. *Rehmannia* contains the vitamins A, B, C, and D, as well as other useful compounds.

*Rehmannia* sp. extracts or extracts of *Rehmannia* sp., including extracts of *Rehmannia* sp. roots or *Rehmannia* sp. root extracts may be obtained commercially from various sources including EUL Herb Manufacturing (La Verne, Calif.) and NuPharma Neutraceuticals (Miami Beach, Fla.). In addition, extracts of *Rehmannia* sp. may be obtained by any of the extraction methods discussed more fully below or known or described in the art.

Siberian ginseng, one of the compounds useful in unique compositions of the present invention, which is also known as *Eleutherococcus senticosus*, is a species of small, woody shrub in the family Araliaceae native to Northeastern Asia. Siberian ginseng is a powerful tonic herb with a wide range of health benefits. For example, Siberian ginseng has immunoprotective effects against breast (mammary gland) carcinoma, stomach carcinoma, oral cavity carcinoma, skin melanoma and ovarian carcinoma. It was found to have a pronounced effect on T lymphocytes, predominantly of the helper/inducer type, but also on cytotoxic and natural killer cells. In addition, Siberian ginseng is known to have a protective effect against osteoporosis. See, e.g., Kropotov et al., "Effects of Siberian ginseng extract and ipriflavone on the development of glucocorticoid-induced osteoporosis." *Bull Exp Biol Med.*, 2002. 133(3):252-4.

As discussed more fully below, the present invention is based in part on the discovery that extracts of Siberian ginseng (or Siberian ginseng extracts) are potent activators of BMP-2 promoter activity, BMP-2 gene expression and BMP-2 protein expression. In addition, the assay results discussed below demonstrate that when extracts of Siberian ginseng are administered in combination with quercetin dihydrate, the combination achieves a surprising synergy resulting in BMP-2 promoter activity, gene expression and protein expression beyond that achieved with either ingredient alone.

Siberian ginseng extracts may be commercially obtained from various suppliers such as Xi'an Tianxingjian Natural Bio-products Group (Xi'an, Shaanxi, China). In addition, Siberian ginseng extract may be obtained using any of the extraction techniques discussed more fully below or known in the art. In one example, a Siberian ginseng extract may be obtained as an alcoholic fluid extraction of the root and/or rhizome of Siberian ginseng.

*Sophora japonica*, or *Sophora fructus japonica*, another of the compounds useful in unique compositions of the present invention, is also referred to as the Pagoda Tree and is native to eastern Asia. Rutin, an active compound that may be found in a *Sophora japonica* extract, may be used to increase the permeability (e.g. the resolution and porousness of the dilation) of capillaries. In addition to rutin, quercetin anhydrate and quercetin dihydrate may be extracted from *Sophora japonica* plants, including from the leaves, stem, flower, seeds, root, etc.

As discussed more fully below, the present invention is based in part on the discovery that extracts of *Sophora japonica* (or *Sophora japonica* extracts) are potent activators of BMP-2 promoter activity, gene expression and protein expression.

*Sophora japonica* extracts may be commercially obtained from various suppliers such as NuPharma Nutraceuticals (Miami Beach, Fla.). In addition, *Sophora japonica* extract may be obtained using any of the extraction techniques discussed more fully below or known in the art. In one example, the ripe seeds of *Sophora japonica* may be used to obtain a *Sophora japonica* extract useful in the present invention.

Licorice extracts, useful in unique compositions of the present invention, are widely used in treating bronchial problems such as catarrh, bronchitis and coughs in general. Licorice also forms an important ingredient in controlling peptic ulcerations, gastritis and ulcers. According to JP 2002 179585 and US 20020009506, when administered in an amount ranging from 50-100 mg per day, licorice can be used to treat osteoporosis, improve bone metabolism, and promote calcification.

As discussed more fully below, the present invention is based in part on the discovery that licorice extracts (or extracts of licorice), for example ethanol and ethanol-water extracts of licorice, are potent activators of BMP-2 promoter activity, gene expression and protein expression. In addition, the assay results discussed below demonstrate that when licorice extract is administered in combination with quercetin dihydrate, the combination achieves a surprising synergy resulting in BMP-2 promoter activity, gene expression and protein expression beyond that achieved with either ingredient alone.

Licorice extracts may be commercially obtained from various suppliers such as Herbs Forever, Inc. (Los Angeles, Calif.). In addition, a licorice extract may be obtained using any of the extraction techniques discussed more fully below or known in the art. In one example, a licorice extract can be an ethanol extract of licorice obtained from the root, runner, and/or rhizome of *Glycyrrhiza glabra*.

Ipriflavone, another of the compounds useful in unique compositions of the present invention, is an isoflavone. Although Ipriflavone may be found in small amounts in legume plants, such as alfalfa, Ipriflavone generally is synthetically manufactured as 7-isopropoxy isoflavone, using polyphenols as a starting material.

As discussed more fully below, the present invention is based in part on the discovery that ipriflavone is a potent inhibitor of RANK-L expression. Ipriflavone may be commercially obtained from various sources. For example, Ostivone® is a synthetic ipriflavone compound available from Technical Sourcing International, Inc. (Missoula, Mont.).

Pomegranates can be extracted to yield an extract of pomegranate (pomegranate extract) that is useful in unique compositions of the present invention. When extracted, pomegranate, known as *Punica granatum*, is generally standardized to ellagic acid or punicalagin content. Punicalagins exist as isomers of 2,3,hexahydroxydiphenoyl-gallagyl-D-glucose. An exemplary structure is shown below:

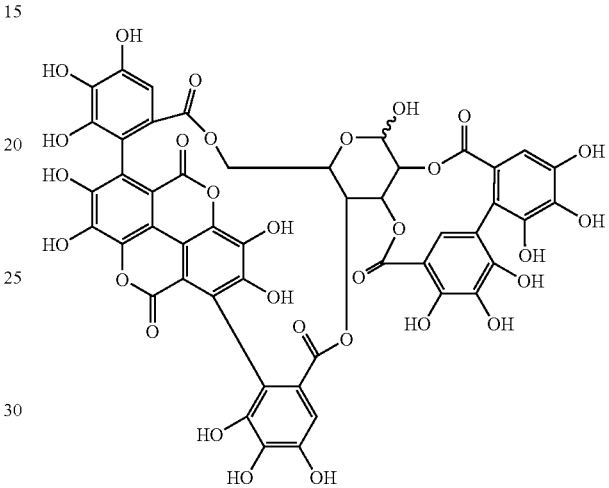

Extracts of pomegranate also may be high in polyphenols, such as hydrolysable tannins, and particularly punicalagins, which may be responsible for the free-radical scavenging ability of pomegranate juice.

In Japan, pomegranate has been used to inhibit bone quantity reduction. See JP 1999 0049884. The present invention is based in part on the discovery that an extract of pomegranate is a potent inhibitor of RANK-L expression, production, or release. In one example, punicalagins present in extracts of pomegranate inhibit or decrease RANK-L expression. Therefore, pomegranate extracts comprising punicalagins, ellagic acid or both are useful in compositions and methods for inhibiting, decreasing, or preventing the production, release, and/or expression of RANK-L.

Pomegranate extracts may be commercially obtained from various sources including Nature's Way (Springville, Utah), Nature's Herbs (American Fork, Utah), Swansen's Health Products (Fargo, N. Dak.) and Doctor's Trust Vitamins (Orlando, Fla.). In addition, a pomegranate extract may be obtained using any of the extraction techniques discussed more fully below or known in the art.

Extracts of *Ginkgo biloba* (or *Ginkgo biloba* extracts), another of the extracts useful in unique compositions of the present invention, are known to have three effects: (1) improve blood flow (including microcirculation in small capillaries) to most tissues and organs; (2) protect against oxidative cell damage from free radicals (antioxidant); and (3) block the effects of platelet aggregation and blood clotting.

*Ginkgo biloba* extracts may be commercially obtained from various sources including Puritan's Pride (Long Island, N.Y.). In addition, *Ginkgo biloba* extracts may be obtained using any of the extraction process disclosed herein or known in the art. For example, *Ginkgo biloba* extracts may be obtained using any of the extraction processes disclosed herein or known in the art to extract dried or fresh leaves, or seeds of Gingko biloba.

Green Tea, which can be extracted to yield one of the compounds useful in unique compositions of the present invention, has long been used by the Chinese as medicine to treat headaches, body aches, poor digestion, and improve well-being and life expectancy. Green tea extract is rich in bioflavonoids, including the anti-oxidant epigallocatechin gallate (EGCG). The EGCG in green tea extract protects against digestive and respiratory infections, blocks the actions of carcinogens, can function as an anti-bacterial, and can also help lower cholesterol levels.

As discussed more fully below, the present invention is based in part on the discovery that green tea extract (or an extract of green tea) is a potent inhibitor of RANK-L expression. Green tea extracts may be commercially obtained from various sources including Life Extension (Fort Lauderdale, Fla.). In addition, a green tea extract may be obtained using any of the extraction techniques discussed more fully below or known in the art.

Grape Seed extracts (or extracts of grape seeds), another of the compounds useful in unique compositions of the present invention, contain a class of flavonoid complexes known as oligomeric proanthocyanidins or OPCs that act as antioxidants (free radical scavengers) in the human body. OPCs may help protect against the effects of internal and environmental stresses (that is, cigarette smoking, pollution, and supporting normal body metabolic processes).

The extracts of grape seed used in the present invention may be obtained from commercially available sources. For example, the grape seed extract may be obtained from Kikkoman Corporation (Tokyo, Japan), Polyphenolics, Inc. (Madera, Calif.), Bio Serae Laboratories SA (Bram, France), OptiPure (Los Angeles, Calif.), Dry Creek Nutrition, Inc. (Modesto, Calif.), or other suitable sources. In addition, the extraction techniques discussed more fully below, or those known or described in the art may be used to produce a grape seed extract to be used in the present invention.

Dong Quai, one of the extract useful in unique compositions of the present invention, also is known as *Angelica sinensis* or "female ginseng" and is an herb from the family Apiaceae, indigenous to China. Its root is commonly known in Chinese as dong quai or danggui (Chinese: 当归; pinyin: dānggui̇̄) and is widely used in Chinese traditional medicine to treat gynecological ailments, fatigue, mild anemia and high blood pressure. Dong Quai has analgesic, anti-inflammatory, antispasmodic and sedative effects. The plant's phytochemicals consist of coumarins, phytosterols, polysaccharides, ferulate, and flavonoids.

Dong Quai extract (or extract of Dong Quai) may be commercially obtained from a variety of different sources, including Capricorns Lair (Ogden, Utah). In addition, Dong Quai can be extracted using any of the extraction techniques described more fully below, or any extraction techniques known in the art.

Although each of the extracts used in the present invention is commercially available, there are numerous extraction methods that can be used to produce an extract to be used in the present invention without commercially purchasing the extract. Some examples of extraction methods that can be used to produce an extract to be used in the present invention are described below. Other examples are known and described in the art, including in various publications and patents. The extraction methods described more fully below are exemplary and one of ordinary skill in the art will appreciate that other extraction techniques and methods may be used to obtain an extract useful in the present invention.

Extracts used in the present invention may be from a variety of sources, including different varieties and species. For example, grape seeds from grapes of any color or variety may be used to obtain a grape seed extract. In addition, any of the parts of a plant may be extracted, including the fruit, peel, seeds, stem, leaves, roots, bark, rhizome, runner, etc.

In one example, an extract useful in the unique compositions of the present invention might be obtained using an organic solvent extraction technique. More specifically, an extract useful in the present invention, such as a licorice extract or a licorice root extract, can be produced by extracting licorice or licorice root with an organic solvent, for example, hexane, ethyl acetate, ethanol, or hydro-ethanol.

In another example, solvent sequential fractionation may be used to obtain an extract useful in the unique compositions of the present invention. For example, using this technique, a grape seed extract could be obtained by sequentially extracting grape seeds with hexane, ethyl acetate, ethanol, and hydro-ethanol. The extracts obtained after each step (fractions) of the sequence will contain chemical compounds in increasing order of polarity similar to the solvents used for extracting them. The fractions are dried to evaporate the solvents, resulting in an extract of grape seed. Those of skill in the art will appreciate that many other solvents can be used in practicing solvent sequential fractionation extraction.

Total hydro-ethanolic extraction techniques might also be used to obtain an extract useful in the unique compositions of the present invention. Generally, this is referred to as a lump-sum extraction. The extract generated in this process will contain a broad variety of phytochemicals present in the extracted material including fat and water solubles. Following collection of the extract solution, the solvent will be evaporated, resulting in the extract. In one example, pomegranates might be extracted using this technique.

Total ethanol extraction may also be used in the present invention. This technique uses ethanol, rather than hydro-ethanol, as the solvent. This extraction technique generates an extract that may include fat soluble and/or lipophilic compounds in addition to water soluble compounds. An extract of green tea might be obtained using this technique.

Another example of an extraction technique that might be used to obtain an extract useful in the present invention is supercritical fluid carbon dioxide extraction (SFE). In this extraction procedure the material to be extracted is not exposed to any organic solvents. Rather, the extraction solvent is carbon dioxide, with or without a modifier, in supercritical conditions (>31.3° C. and >73.8 bar). Those of skill in the art will appreciate that temperature and pressure conditions can be varied to obtain the best yield of extract. This technique generates an extract of fat soluble and/or lipophilic compounds, similar to the total hexane and ethyl acetate extraction technique described above.

Those of skill in the art will appreciate that there are many other extraction processes, both known in the art and described in various patents and publications that can be used to obtain the extracts to be used in practicing the present invention. For example, the extraction procedures described in the following references, which are incorporated herein by reference, could be used in practicing the present invention: Murga et al., "Extraction of natural complex phenols and tannins from grape seeds by using supercritical mixtures of carbon dioxide and alcohol." *J. Agric Food Chem.* 2000 August:48(8):3408-12; Hong et al., "Microwave-assisted extraction of phenolic compounds from grape seed." *Nat Prod Lett.* 2001; 15(3):197-204; Ashraf-Khorassani et al., "Sequential fractionation of grape seeds into oils, polyphenols, and procyanidins via a single system employing $CO_2$-based fluids." *J. Agric Food Chem.,* 2004 May 5; 52(9):2440-4.

Compositions of the Invention

Compositions of the present invention may be formulated in an acceptable carrier and may be prepared, packaged, and labeled for increasing or stimulating bone growth, inhibiting, decreasing, or preventing bone resorption, increasing bone strength, improving bone structure, improving bone architecture, or treatment, prevention, or management of various bone disorders including, but not limited to, fractures, osteoporosis, periodontal disease, metastatic bone disease, and osteolytic bone disease.

In one example, the invention is a composition for increasing or stimulating bone growth, comprising a combination of at least two of the following: quercetin anhydrate, quercetin dihydrate, *Rehmannia* sp. extract, Siberian ginseng extract, *Sophora japonica* extract, licorice extract, and ipriflavone, wherein the combination increases BMP-2 gene or protein expression.

In another example, the invention is a composition for increasing bone growth, comprising a combination of at least two of the following: quercetin, anhydrate, quercetin dihydrate, *Rehmannia* sp. extract, Siberian ginseng extract, *Sophora japonica* extract, licorice extract, and ipriflavone, wherein the combination increases BMP-2 gene or protein expression, and further wherein, if present: quercetin anhydrate or quercetin dihydrate, is present in an amount ranging from approximately 10-1000 mg, more preferably in an amount ranging from approximately 200-750 mg, more preferably in an amount ranging from approximately 300-700 mg, more preferably in an amount ranging from approximately 400-600 mg, more preferably in an amount of approximately 500 mg; *Rehmannia* sp. extract is present in an amount ranging from approximately 10-1000 mg, more preferably in an amount ranging from approximately 100-900 mg, more preferably in an amount ranging from approximately 200-800 mg, more preferably in an amount ranging from approximately 300-700 mg, more preferably in an amount ranging from approximately 400-600 mg, more preferably in an amount of approximately 500 mg; Siberian ginseng extract is present in an amount ranging from 100-800 mg, more preferably in an amount ranging from approximately 200-750 mg, more preferably in an amount ranging from approximately 300-700 mg, more preferably in an amount ranging from approximately 400-600 mg, more preferably in an amount of approximately 500 mg; *Sophora japonica* extract is present in an amount ranging from 10-1000 mg, more preferably in an amount ranging from approximately 100-900 mg, more preferably in an amount ranging from approximately 200-800 mg, more preferably in an amount ranging from approximately 300-700 mg, more preferably in an amount ranging from approximately 400-600 mg, more preferably in an amount of approximately 500 mg; licorice extract is present in an amount ranging from approximately 10-500 mg, more preferably in an amount ranging from approximately 25-450 mg, more preferably in an amount ranging from approximately 50-400 mg, more preferably in an amount ranging from approximately 75-350 mg, more preferably in an amount ranging from approximately more preferably in an amount ranging from approximately 100-300 mg, more preferably in an amount ranging from approximately 125-250 mg, more preferably in an amount ranging from approximately 25-175 mg; and ipriflavone is present in an amount ranging from 200-700 mg, more preferably in an amount ranging from approximately 250-650 mg, more preferably in an amount ranging from approximately 300-600 mg, more preferably in an amount ranging from approximately 400-500 mg, more preferably in an amount of approximately 600 mg.

In another example, the invention is a composition for increasing or stimulating bone growth comprising a combination of quercetin anhydrate, quercetin dihydrate, Siberian ginseng extract, *Sophora japonica* extract, and licorice extract, wherein the combination increases BMP-2 gene or protein expression, and further wherein the quercetin anhydrate or quercetin dihydrate is present in an amount ranging from approximately 10-1000 mg, more preferably in an amount ranging from approximately 200-750 mg, more preferably in an amount ranging from approximately 300-700 mg, more preferably in an amount ranging from approximately 400-600 mg, more preferably in an amount of approximately 500 mg; Siberian ginseng extract is present in an amount ranging from approximately 100-800 mg, more preferably in an amount ranging from approximately 200-750 mg, more preferably in an amount ranging from approximately 300-700 mg, more preferably in an amount ranging from approximately 400-600 mg, more preferably in an amount of approximately 500 mg; *Sophora japonica* extract is present in an amount ranging from approximately 10-1000 mg, more preferably in an amount ranging from approximately 100-900 mg, more preferably in an amount ranging from approximately 200-800 mg, more preferably in an amount ranging from approximately 300-700 mg, more preferably in an amount ranging from approximately 400-600 mg, more preferably in an amount of approximately 500 mg; and licorice extract is present in an amount ranging from 10-500 mg, more preferably in an amount ranging from approximately 25-450 mg, more preferably in an amount ranging from approximately 50-400 mg, more preferably in an amount ranging from approximately 75-350 mg, more preferably in an amount ranging from approximately 100-300 mg, more preferably in an amount ranging from approximately 125-250 mg, more preferably in an amount ranging from approximately 25-175 mg.

In another example, the invention is a composition for increasing or stimulating bone growth comprising a combination of approximately 10-1000 mg of quercetin anhydrate, quercetin dihydrate, more preferably approximately 250-750 mg, more preferably approximately 300-700 mg, more preferably approximately 400-600 mg, more preferably approximately 500 mg; approximately 100-800 mg of Siberian ginseng, more preferably approximately 200-750 mg, more preferably approximately 300-700 mg, more preferably approximately 400-600 mg, more preferably approximately 500 mg; and approximately 10-500 mg of licorice extract, more preferably approximately 25-450 mg, more preferably approximately 50-400 mg, more preferably approximately 75-350 mg, more preferably approximately 100-300 mg, more preferably approximately 125-250 mg, more preferably approximately 25-175 mg, wherein the combination increases BMP-2 gene or protein expression.

In a further example, the invention is a composition for increasing or stimulating bone growth comprising a combination of quercetin anhydrate or quercetin dihydrate, Siberian ginseng extract, and licorice extract, wherein the combination increases BMP-2 gene or protein expression, and further wherein the quercetin anhydrate or quercetin dihydrate, Siberian ginseng extract, and licorice extract are present in equal amounts, more preferably wherein the Siberian ginseng extract is present in an amount that is ½ that of quercetin anhydrate or quercetin dihydrate and the licorice extract is present in an amount that is ⅒ that of quercetin anhydrate or quercetin dihydrate.

In another example, the invention is a composition for increasing or stimulating bone growth comprising a combination of quercetin anhydrate or quercetin dihydrate, and Siberian ginseng extract, wherein quercetin anhydrate or quercetin dihydrate forms approximately 10-75% w/w of the composition, more preferably approximately 50% w/w of the composition and Siberian ginseng extract forms approximately 10-75% w/w of the composition, more preferably approximately 50% w/w of the composition, wherein the combination of quercetin anhydrate or quercetin dihydrate and Siberian ginseng extract increases BMP-2 gene or protein expression.

In yet another example, the invention is a composition for increasing or stimulating bone growth comprising a combination of at least two of: quercetin anhydrate, quercetin dihydrate, Siberian ginseng extract, *Sophora japonica* extract, and licorice extract, wherein if present, quercetin anhydrate or quercetin dihydrate forms approximately 10-75% w/w of the composition, more preferably approximately 50% w/w of the composition; Siberian ginseng extract forms approximately 10-75% w/w of the composition, more preferably approximately 50% w/w of the composition; *Sophora japonica* extract forms approximately 1-50% w/w of the composition, more preferably approximately 2-15% w/w of the composition, more preferably approximately 5-10% w/w of the composition; and licorice extract forms approximately 1-50% w/w of the composition, more preferably approximately 2-15% w/w of the composition, more preferably approximately 5-10% w/w of the composition, further wherein the combination increases BMP-2 gene or protein expression.

In a further example, the invention is a composition for increasing or stimulating bone growth comprising a combination of approximately 10-1000 mg of quercetin anhydrate or quercetin dihydrate, more preferably approximately 250-750 mg, more preferably approximately 300-700 mg, more preferably approximately 400-600 mg, more preferably approximately 500 mg; and approximately 10-500 mg of licorice extract, more preferably approximately 20-125 mg, more preferably approximately 20-100 mg, more preferably approximately 25-75 mg, more preferably approximately 50 mg, wherein the combination increases BMP-2 gene or protein expression.

In another example, the invention is a composition for increasing or stimulating bone growth comprising a combination of approximately 10-1000 mg of quercetin anhydrate or quercetin dihydrate, more preferably approximately 250-750 mg, more preferably approximately 300-700 mg, more preferably approximately 400-600 mg, more preferably approximately 500 mg; and approximately 100-800 mg of Siberian ginseng extract, more preferably approximately 200-750 mg, more preferably approximately 300-700 mg, more preferably approximately 400-600 mg, more preferably approximately 500 mg, wherein the combination of quercetin anhydrate or quercetin dihydrate, and Siberian ginseng extract increases BMP-2 gene or protein expression.

In a further example, the invention is a method of increasing or stimulating bone growth in a subject, comprising administering to the subject a composition comprising a combination of at least two of the following: quercetin anhydrate, quercetin dihydrate, *Rehmannia* sp. extract, *Rehmannia* sp. root extract, Siberian ginseng extract, *Sophora japonica* extract, licorice extract, and ipriflavone, wherein the combination increases BMP-2 gene or protein expression in the subject.

A further example of the invention is a method of increasing or stimulating bone growth in a subject, comprising administering to the subject a composition comprising a combination of approximately 10-1000 mg of quercetin anhydrate or quercetin dihydrate, more preferably approximately 250-750 mg, more preferably approximately 300-700 mg, more preferably approximately 400-600 mg, more preferably approximately 500 mg; approximately 100-800 mg of Siberian ginseng extract, more preferably approximately 200-750 mg, more preferably approximately 300-700 mg, more preferably approximately 400-600 mg, more preferably approximately 500 mg; and approximately 10-500 mg of licorice extract, more preferably approximately 25-450 mg, more preferably approximately 50-400 mg, more preferably approximately 75-350 mg, more preferably approximately 100-300 mg, more preferably approximately 125-250 mg, more preferably approximately 25-75 mg, wherein the combination increases BMP-2 gene or protein expression.

Another example of the invention is a method of increasing or stimulating bone growth in a subject, comprising administering to the subject a composition comprising a combination of approximately 10-1000 mg quercetin anhydrate or quercetin dihydrate, more preferably approximately 250-750 mg, more preferably approximately 300-700 mg, more preferably approximately 400-600 mg, more preferably approximately 500 mg; and approximately 10-500 mg of licorice extract, more preferably approximately 20-125 mg, more preferably approximately 20-100 mg, more preferably approximately 25-75 mg, more preferably approximately 50 mg, wherein the combination increases BMP-2 gene or protein expression.

A further example of the invention is a method of increasing or stimulating bone growth in a subject, comprising administering to the subject a composition comprising a combination of approximately 10-1000 mg quercetin anhydrate or quercetin dihydrate, more preferably approximately 250-750 mg, more preferably approximately 300-700 mg, more preferably approximately 400-600 mg, more preferably approximately 500 mg; and approximately 100-800 mg of Siberian ginseng extract, more preferably approximately 200-750 mg, more preferably approximately 300-700 mg, more preferably approximately 400-600 mg, more preferably approximately 500 mg, wherein the combination of quercetin anhydrate or quercetin dihydrate, and Siberian ginseng extract increases the expression and/or activity of the BMP-2 gene or protein in the subject.

In another example, the present invention is a composition for inhibiting, decreasing, or preventing bone resorption comprising a pomegranate extract and at least one of the following natural, plant-derived extracts: Siberian ginseng extract, *Ginkgo biloba* extract, green tea extract, *Sophora japonica* extract, *Rehmannia* sp. extract, grape seed extract, Dong Quai extract, and ipriflavone, wherein the composition inhibits expression, production, and/or release of RANK-L, and further wherein, the pomegranate extract is present in an amount ranging from approximately 10-2000 mg, more preferably in an amount ranging from approximately 300-1700 mg, more preferably in an amount ranging from approximately 400-1500 mg, more preferably in an amount ranging from approximately 500-1250 mg, more preferably in an amount ranging from approximately 600-1000 mg, more preferably in an amount ranging from approximately 700-900 mg; more preferably in an amount of approximately 500 mg; and if present, Siberian ginseng extract is present in an amount ranging from approximately 100-2000 mg, more preferably in an amount ranging from approximately 300-1700 mg, more preferably in an amount ranging from approximately 400-1500 mg, more preferably in an amount ranging from approximately 500-1250 mg, more preferably in an amount ranging from approximately 600-1000 mg, more preferably in an amount ranging from approximately 700-900 mg; more preferably in an amount of approximately 500 mg; *Ginkgo biloba* extract is present in an amount ranging from approximately 10-1000 mg, more preferably in an amount ranging from approximately 100-900 mg, more preferably in an amount ranging from approximately 200-800 mg, more preferably in an amount ranging from approximately 300-700 mg, more preferably in an amount ranging from approximately 400-600 mg, more preferably in an amount of approximately 500 mg; green tea extract is present in an amount ranging from approximately 300-700, more preferably in an amount ranging from approximately 350-650 mg, more preferably in an amount ranging from approximately 400-600 mg, more preferably in an amount of approximately 500 mg; *Sophora japonica* extract is present in an amount ranging from 10-1000 mg, more preferably in an amount ranging from approximately 100-900 mg, more preferably in an amount ranging from approximately 200-800 mg, more preferably in an amount ranging from approximately 300-700 mg, more preferably in an amount ranging from approximately 400-600 mg, more preferably in an amount of approximately 500 mg; *Rehmannia* sp. extract is present in an amount ranging from approximately 10-1000 mg, more preferably in an amount ranging from approximately 100-900 mg, more preferably in an amount ranging from approximately 200-800 mg, more preferably in an amount ranging from approximately 300-700 mg, more preferably in an amount ranging from approximately 400-600 mg, more preferably in an amount of approximately 500 mg; grape seed extract is present in an amount ranging from 35-250 mg, more preferably in an amount ranging from approximately 50-150 mg, more preferably in an amount ranging from approximately 75-125 mg; Dong quai extract is present in an amount ranging from approximately 10-1000 mg, more preferably in an amount ranging from approximately 100-900 mg, more preferably in an amount ranging from approximately 200-800 mg, more preferably in an amount ranging from approximately 300-700 mg, more preferably in an amount ranging from approximately 400-600 mg, more preferably in an amount of approximately 500 mg; and ipriflavone is present in an amount ranging from approximately 400-700 mg, more preferably in an amount ranging from approximately 450-650 mg, more preferably in an amount ranging from approximately 500-600 mg, more preferably in an amount of approximately 600 mg; wherein the combination inhibits RANK-L expression, production and/or release of RANK-L or inhibits release of calcium from bone.

In a further example, the present invention is a composition for inhibiting, decreasing, or preventing bone resorption comprising a combination of approximately 10-2000 mg of pomegranate extract, more preferably approximately 400-1700 mg, more preferably approximately 500-1500 mg, more preferably approximately 600-1250 mg, more preferably approximately 700-1000 mg, more preferably approximately 800-900 mg; approximately 35-250 mg of grape seed extract, more preferably approximately 50-150 mg, more preferably approximately 75-125 mg; approximately 400-700 mg of ipriflavone, more preferably approximately 450-650 mg, more preferably approximately 500-600 mg, more preferably approximately 600 mg; and approximately 300-700 mg of a green tea extract, more preferably approximately 350-650 mg, more preferably approximately 400-600 mg, more preferably approximately 500 mg, wherein the combination inhibits expression, production, and/or release of RANK-L or inhibits release of calcium from bone.

In another example, the present invention is a composition for inhibiting, decreasing, or preventing bone resorption comprising a combination of approximately 10-2000 mg of pomegranate extract, more preferably approximately 400-1700 mg, more preferably approximately 500-1500 mg, more preferably approximately 600-1250 mg, more preferably approximately 700-1000 mg, more preferably approximately 800-900 mg; approximately 35-250 mg of grape seed extract, more preferably approximately 50-150 mg, more preferably approximately 75-125 mg; and approximately 400-700 mg of ipriflavone, more preferably approximately 450-650 mg, more preferably approximately 500-600 mg, more preferably approximately 600 mg, wherein the combination inhibits expression, production, and/or release of RANK-L or inhibits release of calcium from bone.

In another example, the invention is a composition for inhibiting, decreasing, or preventing bone resorption comprising a combination of pomegranate extract, grape seed extract, and ipriflavone, wherein the grape seed extract is present in an amount of approximately ¹⁄₁₀ the pomegranate extract and the ipriflavone is present in an amount of approximately 400-700 mg, more preferably approximately 450-650 mg, more preferably approximately 500-600 mg, more preferably approximately 600 mg, wherein the combination inhibits expression, production, and/or release of RANK-L or inhibits release of calcium from bone.

In a further example, the invention is a composition for inhibiting, decreasing, or preventing bone resorption comprising a combination of at least two of pomegranate extract, grape seed extract, ipriflavone, and green tea extract, wherein, if present, the pomegranate extract is present in an amount ranging from approximately 25-100% w/w of the composition, more preferably from approximately 30-90% w/w of the composition, more preferably from approximately 40-80% w/w of the composition, more preferably from approximately 45-60% w/w of the composition, more preferably approximately 50% w/w of the composition; the grape seed extract is present in an amount ranging from approximately 1-25% w/w of the composition, more preferably approximately 2-15% w/w of the composition, more preferably approximately 5-10% w/w of the composition; the Ipriflavone is present in an amount ranging from approximately 25-100% w/w of the composition, more preferably from approximately 30-90% w/w of the composition, more preferably from approximately 40-80% w/w of the composition, more preferably from approximately 45-60% w/w of the composition, more preferably approximately 50% w/w of the composition; and the green tea extract is present in an amount ranging from approximately 1-25% w/w of the composition, more preferably approximately 2-15% w/w of the composition, more preferably approximately 5-10% w/w of the composition, further wherein the combination inhibits expression, production, and/or release of RANK-L or inhibits release of calcium from bone.

Another example of the invention is a method of inhibiting, decreasing, or preventing bone resorption in a subject comprising administering to the subject a composition comprising natural, plant-derived extracts, including at least one of the following extracts: pomegranate, Siberian ginseng, *Ginkgo biloba*, green tea, *Sophora japonica, Rehmannia* sp., grape seed, Dong Quai, and ipriflavone, wherein the composition inhibits expression, production, and/or release of RANK-L or inhibits release of calcium from bone.

In a further example, the invention is a method of inhibiting, decreasing, or preventing bone resorption in a subject comprising administering to the subject a composition comprising a combination of approximately 10-2000 mg of pomegranate extract, more preferably approximately 400-1700 mg, more preferably approximately 500-1500 mg, more preferably approximately 600-1250 mg, more preferably approximately 700-1000 mg, more preferably approximately 800-900 mg; approximately 35-250 mg of grape seed extract, more preferably approximately 50-150 mg, more preferably approximately 75-125 mg; approximately 400-

700 mg of ipriflavone, more preferably approximately 450-650 mg, more preferably approximately 500-600 mg, more preferably approximately 600 mg; and approximately 300-700 mg of a green tea extract, more preferably approximately 350-650 mg, more preferably approximately 400-600 mg, more preferably approximately 500 mg, wherein the combination inhibits expression, production, and/or release of RANK-L or inhibits release of calcium from bone.

In a further example, the invention is a method of inhibiting, decreasing, or preventing bone resorption in a subject comprising administering to the subject a composition comprising a combination of approximately 10-2000 mg of pomegranate extract, more preferably approximately 400-1700 mg, more preferably approximately 500-1500 mg, more preferably approximately 600-1250 mg, more preferably approximately 700-1000 mg, more preferably approximately 800-900 mg; approximately 35-250 mg of grape seed extract, more preferably approximately 50-125 mg, more preferably approximately 75-100 mg; and approximately 400-700 mg of ipriflavone, more preferably approximately 450-650 mg, more preferably approximately 500-600 mg, more preferably approximately 600 mg, wherein the combination inhibits expression, production, and/or release of RANK-L or inhibits release of calcium from bone.

In a further example, the invention is a dietary supplement regimen for increasing or stimulating bone growth and inhibiting, decreasing, or preventing bone resorption comprising a first composition comprising a combination of at least two of: quercetin dihydrate, quercetin anhydrate, Siberian ginseng extract, licorice extract, and Sophora japonica extract, wherein the combination of the first composition increases the expression and/or activity of BMP-2; and a second composition comprising a combination of at least two of: pomegranate extract, grape seed extract, ipriflavone, and green tea extract, wherein the combination of the second composition inhibits the expression of RANK-L or inhibits the release of calcium from bones.

In a further example, the invention is a dietary supplement regimen for increasing or stimulating bone growth and inhibiting, decreasing, or preventing bone resorption comprising a first composition comprising a combination of at least two of: quercetin anhydrate, quercetin dihydrate, Siberian ginseng extract, licorice extract, and Sophora japonica extract, wherein, if present, quercetin anhydrate or quercetin dihydrate is present in an amount ranging from approximately 10-1000 mg, more preferably in an amount ranging from approximately 200-750 mg, more preferably in an amount ranging from approximately 300-700 mg, more preferably in an amount ranging from approximately 400-600 mg, more preferably in an amount of approximately 500 mg; wherein, if present, Siberian ginseng extract is present in an amount ranging from approximately 100-800 mg, more preferably in an amount ranging from approximately 200-750 mg, more preferably in an amount ranging from approximately 300-700 mg, more preferably in an amount ranging from approximately 400-600 mg, more preferably in an amount of approximately 500 mg; wherein, if present, licorice extract is present in an amount ranging from 10-500 mg, more preferably in an amount ranging from approximately 25-450 mg, more preferably in an amount ranging from approximately 50-400 mg, more preferably in an amount ranging from approximately 75-350 mg, more preferably in an amount ranging from approximately 100-300 mg, more preferably in an amount ranging from approximately 125-250 mg, more preferably in an amount ranging from approximately 25-175 mg; and wherein if present, Sophora japonica extract is present in an amount ranging from approximately 10-1000 mg, more preferably in an amount ranging from approximately 100-900 mg, more preferably in an amount ranging from approximately 200-800 mg, more preferably in an amount ranging from approximately 300-700 mg, more preferably in an amount ranging from approximately 400-600 mg, more preferably in an amount of approximately 500 mg, and further wherein the combination of the first composition increases the expression and/or activity of BMP-2; and a second composition comprising a combination of at least two of: pomegranate extract, grape seed extract, ipriflavone, and green tea extract, wherein, if present, pomegranate extract is present in an amount ranging from approximately 10-2000 mg, more preferably approximately 400-1700 mg, more preferably approximately 500-1500 mg, more preferably approximately 600-1250 mg, more preferably approximately 700-1000 mg, more preferably approximately 800-900 mg; wherein, if present, grape seed extract is present in an amount ranging from approximately 35-250 mg, more preferably approximately 50-150 mg, more preferably approximately 75-125 mg; wherein, if present, ipriflavone is present in an amount ranging from approximately 400-700 mg, more preferably approximately 450-650 mg, more preferably approximately 500-600 mg, more preferably approximately 600 mg; and wherein, if present, green tea extract is present in an amount ranging from approximately 300-700 mg, more preferably approximately 350-650 mg, more preferably approximately 400-600 mg, more preferably approximately 500 mg, and further wherein the combination of the second composition inhibits the expression of RANK-L or inhibits the release of calcium from bones.

Modes of Administration

The compositions of the invention may be administered systemically or locally. For systemic use, the compositions of the invention are formulated for parenteral (e.g., intravenous, subcutaneous, intramuscular, intraperitoneal, intranasal or transdermal) or enteral (e.g., oral or rectal) delivery according to conventional methods. Intravenous administration can be by a series of injections or by continuous infusion over an extended period. Administration by injection or other routes of discretely spaced administration can be performed at intervals ranging from weekly to once to three times daily. Alternatively, the compositions disclosed herein may be administered in a cyclical manner (administration of disclosed composition; followed by no administration; followed by administration of disclosed composition; and the like). Treatment can continue until the desired outcome is achieved. Alternatively, administration of the compositions of the present invention may be continual, and thereby be a preventative administration, rather than an administration for treatment.

In general, compositions of the present invention can include a cosmetically or pharmaceutically acceptable vehicle, such as saline, buffered saline, 5% dextrose in water, borate-buffered saline containing trace metals or the like. Compositions of the present invention may further include one or more excipients, for example, vitamin A, vitamin D, or calcium; preservatives; solubilizers; buffering agents; albumin to prevent protein loss on vial surfaces; lubricants; fillers; stabilizers; etc. Methods of formulation are well known in the art and are disclosed, for example, in Remington's Pharmaceutical Sciences, Gennaro, Mack Publishing Co., Easton Pa., 1990, which is incorporated herein by reference.

Compositions for use within the present invention can be in the form of sterile, non-pyrogenic liquid solutions or suspensions, coated capsules, suppositories, lyophilized powders, transdermal patches or other forms known in the art. Local administration may be by injection at the site of injury or defect, or by insertion or attachment of a solid carrier at the site, or by direct, topical application of a viscous liquid, or the like. For local administration, the delivery vehicle preferably provides a matrix for the growing bone or cartilage, and more preferably is a vehicle that can be absorbed by the subject without adverse effects.

Aqueous suspensions may contain the extract ingredients of the present invention in admixture with pharmacologically acceptable excipients such as vitamin A, vitamin D, and calcium, suspending agents, such as methyl cellulose; and wetting agents, such as lecithin, lysolecithin or long-chain fatty alcohols. The said aqueous suspensions may also contain preservatives, coloring agents, flavoring agents, sweetening agents and the like in accordance with industry standards.

Preferably, compositions of the present invention are orally administered in the form of a pill, tablet, powder, bar, food, beverage, lozenge, etc. Additionally, compositions of the present invention may be presented as a dried or powdered product for reconstitution with water or other suitable vehicle before use. Liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid).

When administered in the form of a beverage, compositions of the present invention may be water-based, milk-based, tea-based, fruit juice-based, or some combination thereof.

Compositions of the present invention may also be orally administered in the form of a solid prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The solids may be coated by methods well-known in the art. In a preferred embodiment, the composition of the present invention may take the form of a two-piece hard shell capsule, a soft gelatin capsule, or a powder to be dissolved in a liquid for oral consumption. Preparations for oral administration may be suitably formulated to give controlled release of the active compound.

Compositions of the present invention that are orally administered can further comprise thickeners, including xanthum gum, carboxymethyl-cellulose, carboxyethyl-cellulose, hydroxypropyl-cellulose, methyl-cellulose, microcrystalline cellulose, starches, dextrins, fermented whey, tofu, maltodextrins, polyols, including sugar alcohols (e.g., sorbitol and mannitol), carbohydrates (e.g. lactose), propylene glycol alginate, gellan gum, guar, pectin, tragacanth gum, gum acacia, locust bean gum, gum arabic, gelatin, as well as mixtures of these thickeners. These thickeners are typically included in the formulations of the present invention at levels up to about 0.1%, depending on the particular thickener involved and the viscosity effects desired.

Orally administered compositions of the present invention can, and typically will, contain an effective amount of one or more sweeteners, including carbohydrate sweeteners and natural and/or artificial no/low calorie sweeteners. The amount of the sweetener used in the formulations of the present invention will vary, but typically depends on the type of sweetener used and the sweetness intensity desired.

In addition to the formulations described previously, the compounds may also be a formulated as a sustained and/or timed release formulation. Common timed and/or controlled release delivery systems include, but are not be restricted to, starches, osmotic pumps, or gelatin micro capsules.

The compositions may, if desired, be presented in a pack or dispenser device which may comprise one or more unit dosage forms comprising a composition of the present invention. The pack may for example comprise metal or plastic foil, such as a blister pack. The pack or dispenser device may be accompanied by instructions for administration.

Preparations of compositions of the present invention for topical and local application comprise aerosol sprays, lotions, gels and ointments in cosmetically or pharmaceutically appropriate vehicles which may comprise lower aliphatic alcohols, polyglycols such as glycerol, polyethylene glycol, esters of fatty acids, oils and fats, and silicones. The preparations may further comprise antioxidants, such as ascorbic acid or tocopherol, and preservatives, such as p-hydroxybenzoic acid esters.

Parenteral preparations comprise particularly sterile or sterilized products.

Injectable compositions may be provided containing a combination of the extracts of the present invention and any of the well known injectable carriers. These may contain salts for regulating the osmotic pressure.

Other useful dosage forms can be prepared by methods and techniques that will be well understood by those of skill in the art and may include the use of additional ingredients in producing tablets, capsules, or liquid dosage forms. Although exemplary dosages, dose frequencies, and methods of administration are discussed herein, these are merely exemplary and it is appreciated that the dose, dose frequency, and mode of administration may vary according to the age, body weight, condition and response of the individual consumer or patient, and the particular composition of the present invention that is used.

EXAMPLES

It is not the policy of applicants to engage in animal testing. However, applicants obtained significant results through in vitro testing of potential ingredients to be used in compositions and methods of the present invention, and although in vitro tests can provide useful information, such tests cannot replace animal studies because bone, as an organ, together with the complex mechanisms controlling it, cannot be mimicked in the laboratory. Therefore, Applicants performed several animal studies, described below, to confirm the activity of compositions and methods useful in the present invention. In performing all animal studies, Applicants followed the guidance for handling and humane treatment of animals as outlined, for example, in the Guidelines for Preclinical and Clinical Evaluation of Agents Used in the Prevention or Treatment of Postmenopausal Osteoporosis, published April, 1994 by the Food and Drug Administration, Division of Metabolic and Endocrine Drug Products, the entire contents of which are incorporated herein by reference. See also Guidelines for Preclinical Evaluation and Clinical Trials in Osteoporosis published by the World Health Organization in 1998 (ISBN number 9789241545228) and Wark, John D. and Westmore, Ann, Studies of drugs and other measures to prevent and treat osteoporosis; a guide for non-experts, available at www.who.int/entity/ageing/publications/noncommunicable/alc_osteoporosis_brief.pdf—(last visited Oct. 21, 2007), the entire contents of which are incorporated by reference herein.

Example 1

Expression/Activity of BMP-2 Promoter, Gene, and Protein

2T3-BMP2-Luciferase cells, which are murine fibroblast cells transfected with BMP-2 promoters linked to the reporter gene luciferase, are cultured using alpha-MEM 10% FCS with 1% penicillin/streptomycin and 1% glutamine and are split ⅕ once per week. The cells are plated in microtiter plates at a cell density of $5\times10^3$ cells/100 µl/well. The cells are allowed to adhere and stabilize using a preincubation period of 24 hrs at 37° C. with 5% $CO_2$. The media is removed and replaced with 50 µl of alpha-MEM 4% FCS. 50 µl of Serum Free (0.1% BSA) containing the compound or factor (2×) to be tested is added to each well. The final volume is 100 ul and the final serum concentration is 2% FCS. A routine positive control used is recombinant human BMP2 ("rhBMP2") or Chinese Hamster Ovary-BMP2 ("CHO-BMP2") conditioned media. The treated cells are then incubated at 37° C., 5% $CO_2$ for 48 hrs. Media is then removed and the cells are rinsed 3 times with PBS. Excess PBS is removed from the wells and 100 µl of cell culture lysing reagent (Promega #E153A) is added to each well and incubated for at least 10 min. 10 µl of the cell lysate is added to a 96 well white luminometric plate (Dynatech Labs #0010107100) containing 100 µl of luciferase assay buffer with substrate (Promega #E152A). The luciferase activity is read using a Dynatech ML2250 automated 96 well luminometer. The data is then expressed as either percentage of luciferase activity/well or percentage of luciferase activity/ µg protein.

The following compounds were tested for their ability to activate the BMP-2 promoter: quercetin, *Rehmannia* sp. extract, *Rehmannia* sp. root extract, Siberian ginseng extract, *Sophora japonica* extract, licorice extract, ipriflavone, and cal-z-bone. The results and concentrations tested are reported below at Table 1:

MEM (as recommended by ATCC) at 37° C. and 5% $CO_2$. Twenty-four hours prior to experimentation, $3\times10^5$ cells are seeded in 12-well plates in phenol-red free MEM. For each experiment, cells are treated with test extracts at treatment concentrations of 10, 1, and 0.1 µg/ml. After an overnight incubation, RNA is extracted using conventional trizol/ guanidine isothiocyanate based lysis. The isolated RNA was digested with RNase-free DNase I to remove any DNA contamination and then reverse transcribed to cDNA using random hexamer as well as oligo(dT) primers according to the manufacturer's instructions (Stratagene). Quantitative real time PCR is performed using FAM-labeled specific primers for BMP-2 and HEX-labeled specific primers for 18S rRNA (Invitrogen). All reactions are carried out in triplicate and the relative amount of mRNAs in treated versus untreated samples is calculated using the comparative CT method established by Applied Biosystems (2001). Gene expression changes of 2-fold or greater are considered significant.

To measure BMP-2 protein expression, Hu09 cells are plated in 96-well culture plates at the density of $1\times10^4$ cells/well and cultured with alpha-MEM supplemented with 10% FCS for 24 hours. The cells are treated with different proteasome inhibitors for 24 hours. After incubation, the conditioned media is transferred into microcentrifuge tubes and centrifuged at 14,000 rpm for 2-3 minutes to remove cellular debris. The concentration of BMP-2 protein in the supernatant is then determined using the standard BMP-2 Elisa Kit (R&D ELISA KIT DBP200). Recombinant hBMP-2 (R&D) is used as a standard.

The following compounds were tested for their ability to increase the expression of BMP-2 gene expression and

TABLE 1

| | BMP2 Promoter assay (ratio to control) | | | | | | | | | |
|---|---|---|---|---|---|---|---|---|---|---|
| Conc. µg/ml | R-1 | R-2 | R-3 | SFJ | SJ FOLD* | SG | Q | I | L | CZB |
| 100 | 1.00 | 0.90 | 0.80 | 2.00 | 0.80 | 1.10 | 5.20 | 4.50 | 1.40 | 0.90 |
| 50 | 0.90 | 0.90 | 0.90 | 1.60 | 0.70 | 0.90 | 4.80 | 4.40 | 1.40 | 0.90 |
| 25 | 0.90 | 1.10 | 0.95 | 1.00 | 0.84 | 1.30 | 3.60 | 3.90 | 1.00 | 1.10 |
| 12.5 | 0.90 | 1.30 | 0.93 | 1.00 | 0.77 | 1.20 | 2.90 | 3.60 | 0.80 | 1.90 |
| 6.3 | 1.00 | 1.10 | 0.88 | 0.90 | 0.87 | 1.30 | 2.30 | 2.90 | 0.80 | 1.40 |
| 3.2 | 1.10 | 1.10 | 0.93 | 0.90 | 0.87 | 1.40 | 1.80 | 2.10 | 0.90 | 1.10 |
| 1.6 | 1.00 | 1.20 | 0.95 | 1.40 | 0.88 | 1.20 | 1.30 | 1.50 | 0.70 | 1.30 |
| 0.8 | 1.10 | 1.10 | 0.98 | 0.90 | 0.85 | 1.20 | 1.15 | 1.20 | 0.80 | 1.20 |
| 0.4 | 0.90 | 1.00 | 0.99 | 0.90 | 0.85 | 1.10 | 1.00 | 0.90 | 0.80 | 1.20 |
| 0.2 | 1.00 | 0.90 | 0.86 | 0.90 | 0.79 | 1.20 | 1.10 | 1.00 | 0.80 | 1.10 |
| 0.1 | 0.90 | 0.90 | 0.87 | 0.80 | 0.82 | 1.10 | 1.10 | 0.90 | 1.20 | 1.10 |
| 0.05 | 0.80 | 0.90 | 1.08 | 1.20 | 0.84 | 1.00 | 1.00 | 1.00 | 0.70 | 1.10 |

In Table I,
R-1 = *Rehmannia* sp. extract (EUL),
R-2 = *Rehmannia* sp. extract (Draco),
R-3 = *Rehmannia* sp. root (NuPharma),
SFJ = *Sophora fructus japonica*,
SJ = *Sophora japonica* (NuPharma),
SG = Siberian *ginseng*,
Q = Quercetin,
I = Ipriflavone,
L = Licorice,
CZB = Cal-Z-bone.
*Note: If the fold value is 2 or greater, the treatment significantly activated BMP-2 promoter. If the fold value is less than 2, the treatment had no effect on BMP-2 promoter. Thus, according to this assay, quercetin dihydrate and ipriflavone were the most potent activators of the BMP-2 promoter.

It is also possible to test for BMP-2 gene expression and protein expression using assays similar to those described above for testing BMP-2 promoter activity. In particular, for gene expression, the human osteosarcoma cell line, MG-63 (ATCC# CRL-1427), is maintained in phenol-red containing protein expression: quercetin, *Rehmannia* sp. extract, *Rehmannia* sp. root extract, Siberian ginseng extract, *Sophora japonica* extract, licorice extract, ipriflavone, and cal-z-bone. The results and concentrations tested in the protein expression assay are reported below in Table 2.

TABLE 2

BMP-2 Protein Expression Assay

| Conc. µg/ml | R-1 | R-2 | R-3 | SFJ | SJ | SG | Q | I | L | CZB |
|---|---|---|---|---|---|---|---|---|---|---|
| | | | | | FOLD* | | | | | |
| 100 | <1.3 | <1.3 | <1.3 | 3.0 | <1.3 | 2.4 | 2.2 | 1.8 | <1.3 | <1.3 |
| 10 | <1.3 | <1.3 | <1.3 | 3.0 | <1.3 | 3.4 | 4.6 | 1.8 | <1.3 | <1.3 |
| 1 | <1.3 | <1.3 | <1.3 | 2.2 | <1.3 | 2.0 | 2.0 | 2.4 | <1.3 | <1.3 |
| 0 | 1.0 | 1.0 | 1.0 | 1.0 | 1.0 | 1.0 | 1.0 | 1.0 | 1.0 | 1.0 |

In Table 2,
R-1 = *Rehmannia* sp. extract (EUL),
R-2 = *Rehmannia* sp. extract (Draco),
R-3 = *Rehmannia* sp. root (NuPharma),
SFJ = *Sophora fructus japonica*,
SJ = *Sophora japonica* (NuPharma),
SG = Siberian *ginseng*,
Q = Quercetin,
I = Ipriflavone,
L = Licorice, and
CZB = Cal-Z-bone.
*Note: If the fold value is 2 or greater, the treatment significantly activated BMP-2 protein expression. If the fold value is less than 2, the treatment had no effect on BMP-2 protein expression.

The results and concentrations tested in the gene expression assay are listed below in Table 3. An increase in gene expression that is a change of 2-fold or greater is considered significant.

TABLE 3

BMP-2 Gene Expression Assay, 10 µg/ml

| Test Ingredient: | Fold Change in Gene Expression: |
|---|---|
| *Rehmannia* sp. extract (EUL) | 28 × increase |
| *Rehmannia* sp. extract (Draco) | 11.7 × increase |
| *Rehmannia* sp. root (NuPharma) | 6.3 × increase |
| *Sophora fructus japonica* | 49 × increase |
| *Sophora japonica* (NuPharma) | 8.3 × increase |
| Siberian ginseng | 27 × increase |
| Quercetin | 2.6 × increase |
| Ipriflavone | No effect |
| Licorice | 45 × increase |

Additional results of the gene expression assay are listed below in Table 4. In Table 4, Q=quercetin, SG=Siberian ginseng, SJ=*Sophora japonica*, and L=licorice. An increase in gene expression that is 2-fold or greater is considered significant. Synergy was found at a 10:5 or 2:1 and 10:10 or 1:1 ratio of quercetin to licorice over quercetin alone.

TABLE 4

BMP-2 Gene Expression Assay

| Ingredient (dosage): | N | BMP-2 Expression (fold change) |
|---|---|---|
| Q (100 µg/ml) | 1 | 14 |
| Q (20 µg/ml) | 2 | 4.61 ± 0.07 |
| Q (10 µg/ml) | 1 | 5 |
| Q (10 µg/ml) | 2 | 3.48 ± 0.08 |
| Q (10 µg/ml) | 2 | 3.54 ± 0.12 |
| Q (10 µg/ml) | 2 | 3.52 ± 0.12 |
| Q (5 µg/ml) | 2 | 2.51 ± 0.14 |
| Q (1 µg/ml) | 1 | 2 |
| Q (1 µg/ml) | 1 | 2.03 |
| Q (0.1 µg/ml) | 1 | No change (−1.06) |
| SG (10 µg/ml) | 2 | 11.26 ± 0.14 |
| SG (10 µg/ml) | 2 | 12.38 ± 1.00 |
| SG (1 µg/ml) | 2 | 5.61 ± 1.45 |
| SG (0.1 µg/ml) | 2 | 2.58 ± 0.38 |
| SJ (10 µg/ml) | 2 | 29.10 ± 2.71 |
| SJ (10 µg/ml) | 2 | 32.45 ± 0.32 |
| SJ (10 µg/ml) | 2 | 32.80 ± 1.12 |
| SJ (5 µg/ml) | 2 | 23.43 ± 0.23 |
| SJ (2.5 µg/ml) | 2 | 14.89 ± 0.95 |
| SJ (1 µg/ml) | 2 | 11.64 ± 2.04 |
| SJ (0.1 µg/ml) | 2 | 3.72 ± 0.37 |
| L (100 µg/ml) | 1 | 29 |
| L (10 µg/ml) | 1 | 8 |
| L (1 µg/ml) | 1 | 4 |
| Q + SG (10 µg/ml each) | 2 | No change (0.07 ± 1.82) |
| Q + SG (10 µg/ml each) | 1 | No change (1.36) |
| Q + SJ (10 µg/ml each) | 2 | 12.01 ± 0.76 |
| Q (10 µg/ml) + SJ (1 µg/ml) | 2 | 7.09 ± 0.75 |
| Q (10 µg/ml) + SJ (0.1 µg/ml) | 2 | 2.63 ± 0.15 |
| Q (1 µg/ml) + SJ (10 µg/ml) | 2 | No change (1.30 ± 0.17) |
| Q (5 µg/ml) + SJ (2.5 µg/ml) | 2 | 4.07 ± 0.02 |
| Q (10 µg/ml) + SJ (5 µg/ml) | 2 | 13.86 ± 1.22 |
| Q (20 µg/ml) + SJ (10 µg/ml) | 2 | 16.86 ± 0.41 |
| SG (10 µg/ml) + SJ (10 µg/ml) | 2 | 1.97 ± 0.62 |
| SG (10 µg/ml) + SJ (1 µg/ml) | 2 | 3.36 ± 0.53 |
| SG (10 µg/ml) + SJ (0.1 µg/ml) | 2 | 4.57 ± 0.87 |
| Q (100 µg/ml) + L (100 µg/ml) | 1 | 38 |
| Q (100 µg/ml) + L (10 µg/ml) | 1 | 252 |
| Q (100 µg/ml) + L (1 µg/ml) | 1 | 35 |
| Q (10 µg/ml) + L (100 µg/ml) | 1 | 92 |
| Q (10 µg/ml) + L (10 µg/ml) | 1 | 71 |
| Q (10 µg/ml) + L (1 µg/ml) | 1 | 15 |
| Q (1 µg/ml) + L (100 µg/ml) | 1 | 31 |
| Q (1 µg/ml) + L (10 µg/ml) | 1 | 37 |
| Q (1 µg/ml) + L (1 µg/ml) | 1 | 6 |
| Q + SG + SJ (10 µg/ml each) | 2 | No change (1.39 ± 0.26) |
| Q (0 µg/ml) | 3 | 1.01 ± 0.05 |
| Q (10 µg/ml) | 3 | 7.22 ± 0.51 |
| L (0 µg/ml) | 3 | 1.01 ± 0.05 |
| L (1 µg/ml) | 3 | 1.34 ± 0.12 |
| L (5 µg/ml) | 3 | 0.81 ± 0.03 |
| L (10 µg/ml) | 3 | 1.04 ± 0.04 |
| Q (10 µg/ml) + L (1 µg/ml) | 3 | 8.54 ± 2.19 |
| Q (10 µg/ml) + L (5 µg/ml) | 3 | 13.50 ± 4.49 |
| Q (10 µg/ml) + L (10 µg/ml) | 3 | 14.77 ± 3.04 |

Example 2

Calvarial Assay to Measure Bone Growth

Neonatal murine calvaria from 4 day old Swiss white mice are excised, placed into BGJ media (Sigma), and cut in half along the midline suture. One milliliter of BGJ media supplemented with 0.1% bovine serum albumin (BSA) is added to each well of a 12 well tissue culture plate (Costar) to which the relevant factors or vehicles are added. Each half calvaria is placed on a stainless steel grid in the above media at the media/air interface. Usually 4 bones per experimental group are used. Recombinant BMP-2 (5 µg/ml), FGF (100 ng/ml) or insulin (10 µg/ml) can be used as a positive stimulator of bone formation. Factors to be tested are added on Day 0 (the day of dissection) and media is changed at 24 and 96 hours (if a 7 day assay is required). Calvaria are maintained in humidified air (5% Co2), at 37° C. Following the period of incubation, the calvaria are then removed and fixed overnight in 10% formalin. The calvaria are then decalcified in 14% EDTA overnight and are then embedded in paraffin wax. Sections are then cut, using a standard microtome, along the midline suture to reveal the coronal suture and the region posterior to this suture. Four micrometer sections were taken initially and at two sequential 400 nm depths. Sections are placed on coated glass slides (Superfrost plus, Fisher Scientific, Pittsburgh, Pa.) and stained with hematoxylin and eosin. The total and new bone area (expressed as mm$^2$), suture thickness (mm), and number of cells lining the bone surface are determined in the section posterior to the sagittal suture. Histomorphometric analysis is performed using the Osteomeasure System (Osteometrics INC, Atlanta, Ga.).

The extracts tested in this assay include *Sophora fructus japonica* extract, Siberian ginseng extract, quercetin dihydrate, quercetin anhydrate, ipriflavone, licorice, and Cal-Z-bone. The results of testing these extracts in the calvarial assay are reported below in Tables 5 and 6. In Table 5, SJ=*Sophora fructus japonica*, SG=Siberian Ginseng, Q=Quercetin, I=Ipriflavone, L=Licorice, and CZB=Cal-Z-Bone. BMP-2 and Simvastatin were used as positive controls. In the below table, superscript a ($^a$) means that the result is significantly different (p<0.05) to the blank sample (concentration at 0 µg/ml). Differences with p≤0.05 (i.e. where the margin of error is less than or equal to 5%) are considered significant. The first four lines of data on Table 5 are based on mixtures of various ratios of the ingredients, e.g. 1:1 under "Q:SG" indicates that the quercetin dihydrate and Siberian ginseng ingredients are present in that mixture at the same amounts.

Significantly, the above results indicate that the synergy between quercetin and Siberian ginseng extract is more than additive. Specifically, assuming an additive effect, at 1 µg/ml new bone formation of approximately 12 mm$^2$×10 mm$^{-3}$ would be expected. Therefore, at fifty percent concentration of quercetin and Siberian ginseng extract, the expected result would be approximately 6 mm$^2$×10$^{-3}$ but the above results show that the combination of quercetin and Siberian ginseng extract achieved new bone formation of approximately 13 mm$^2$×10$^{-3}$.

The calvarial assay described above was repeated with various combinations of the extracts useful in compositions of the present invention. For Table 6, Q=quercetin, SG=Siberian ginseng, L=licorice. In the below table, superscript a ($^a$) means that the result is significantly different (p<0.05) to the blank sample (concentration at 0 µg/ml). Differences with p<0.05 are considered significant. The results for each formulation are reported below in Table 6.

TABLE 5

Calvarial Assay Results- Bone formation

| µg/ml | Q:SG 1:1 | Q:SJ 10:1 | Q:SG:SJ 10:10:1 | Q:L 10:1 mm$^2$ × 10$^{-3}$ | Q:SJ:L 10:01:1 | Q:SG:L 10:10:1 | Q:SG:SJ:L 10:5:1:1 |
|---|---|---|---|---|---|---|---|
| 100 | 0.10 ± 0.12 | 0.10 ± 0.15 | 0.10 ± 1.20 | 0.10 ± 0.15 | 0.10 ± 0.15 | 0.10 ± 0.15 | 0.10 ± 0.15 |
| 10 | 11.40 ± 1.15$^a$ | 0.10 ± 0.15 | 412.70 ± 0.86$^a$ | 8.22 ± 2.09 | 3.52 ± 0.75 | 13.10 ± 1.18$^a$ | 13.80 ± 2.49$^a$ |
| 1 | 13.00 ± 1.30$^a$ | 7.16 ± 1.39 | 12.10 ± 1.71$^a$ | 10.20 ± 3.52 | 12.50 ± 1.60$^a$ | 11.70 ± 1.28$^a$ | 9.85 ± 1.51 |
| 0 | 5.65 ± 0.36 | 5.65 ± 0.36 | 5.65 ± 0.36 | 6.73 ± 0.58 | 6.73 ± 0.58 | 6.73 ± 0.58 | 6.51 ± 0.58 |

| µg/ml | SFJ | SG | Q | I Mm$^2$ × 10$^{-3}$ | L | CZB |
|---|---|---|---|---|---|---|
| 100 | 6.19 ± 0.74 | 5.42 ± 0.54$^a$ | 13.55 ± 1.47$^a$ | 7.04 ± 0.69$^a$ | 7.31 ± 0.68 | 6.12 ± 0.92 |
| 10 | 7.48 ± 0.92$^a$ | 5.43 ± 1.03$^a$ | 13.41 ± 2.50$^a$ | 6.05 ± 1.12 | 5.99 ± 2.05 | 6.02 ± 0.774 |
| 1 | 7.02 ± 0.98 | 4.80 ± 0.83$^a$ | 7.57 ± 1.52 | 2.44 ± 0.66 | 9.08 ± 0.89$^a$ | 8.84 ± 1.35$^a$ |
| 0 | 4.13 ± 0.62 | 1.90 ± 0.43 | 3.93 ± 0.80 | 3.74 ± 0.42 | 3.83 ± 0.42 | 3.73 ± 0.42 |

| Conc. µg/ml | BMP2 mm$^2$ × 10$^{-3}$ | Conc. µM | Simvastatin mm$^2$ × 10$^{-3}$ |
|---|---|---|---|
| 50 | 8.50 ± 1.20 | 1 | 12.5 ± 1.00 |
| 0.5 | | 0.5 | 9.50 ± 1.00 |
| 0.25 | | 0.25 | 7.45 ± 1.34 |
| 0 | 5.90 ± 1.20 | 0 | 5.90 ± 0.60 |

TABLE 6

Calvarial Assay Results - Bone Formation Stimulated by Extract Combinations

| Conc. Q ug/ml | mm² × 10⁻³ | Conc. SG ug/ml | mm² × 10⁻³ | Conc. L ug/ml | mm² × 10⁻³ | Conc. ug/ml | Q:SG 2.5:1 Mm² × 10⁻³ | Q:SG 5:1 | Q:L 2.5:1 | Q:L 5:1 |
|---|---|---|---|---|---|---|---|---|---|---|
| 14.3 | 0.10 ± 0.12 | 5.7 | 7.90 ± 0.54[a] | 10 | 9.80 ± 0.45[a] | 20 | 0.10 ± 0.12 | 0.10 ± 0.12 | 0.10 ± 0.12 | 0.10 ± 0.12 |
| 8.3 | 0.10 ± 0.10 | 1.7 | 9.56 ± 0.67[a] | 5.7 | 10.45 ± 0.65[a] | 10 | 0.10 ± 0.10 | 0.10 ± 0.10 | 0.50 ± 0.32 | 0.10 ± 0.10 |
| 0.7 | 10.30 ± 0.78[a] | 0.3 | 8.60 ± 0.78[a] | 1.7 | 11.56 ± 0.80[a] | 1 | 7.80 ± 0.67[a] | 9.60 ± 0.89[a] | 8.32 ± 0.87[a] | 6.40 ± 0.78 |
| 0 | 4.40 ± 0.52 | 0 | 4.40 ± 0.52 | 0.3 | 8.60 ± 0.67[a] | 0 | 4.80 ± 0.32 | 4.80 ± 0.12 | 5.20 ± 0.25 | 5.20 ± 0.25 |
|  |  |  |  | 0 | 4.20 ± 0.45 |  |  |  |  |  |

| Conc. ug/ml | Q + L Q at constant, 1 ug/ml mm² × 10⁻³ | Conc. ug/ml | Q + L Q at constant, 0.2 ug/ml mm² × 10⁻³ | Conc. ug/ml | Q + L L at constant, 2 ug/ml mm² × 10⁻³ | Conc. Ug/ml | Q + L L at constant, 0.2 ug/ml mm² × 10⁻³ |
|---|---|---|---|---|---|---|---|
| Q-1, L-2 | 6.59 ± 1.54 | Q-0.2, L-2 | 10.10 ± 1.52[a] | L-2, Q-1 | 15.30 ± 2.41[a] | L-0.2, Q-1 | 12.60 ± 1.70[a] |
| Q-1, L-0.5 | 10.30 ± 2.00 | Q-0.2, L-0.5 | 6.41 ± 1.11 | L-2, Q-0.2 | 13.90 ± 0.42[a] | L-0.2, Q-0.2 | 13.20 ± 0.77[a] |
| Q-1, L-0.125 | 12.80 ± 4.42 | Q-0.2, L-0.125 | 7.04 ± 1.31 | L-2, Q-0.625 | 11.10 ± 0.38[a] | L-0.2, Q-0.625 | 10.30 ± 1.27[a] |
| Q-1 | 13.70 ± 3.20[a] | Q-0.2 ug/ml | 6.90 ± 0.56 | L-2 ug/ml | 9.10 ± 0.45[a] | L-0.2 ug/ml | 6.80 ± 0.76 |
| Q-0 ug/ml | 6.23 ± 0.84 | Q-0 ug/ml | 6.15 ± 0.68 | L-0 ug/ml | 6.27 ± 0.34 | L-0 ug/ml | 6.54 ± 0.65 |

Example 3

In Vivo Study to Measure Bone Growth

Three different formulas were tested in an in vivo study involving female, intact rats, aged approximately 12-14 weeks, with approximate body weights between 200-250 grams. Formula 1 included dosages of quercetin anhydrate and licorice at 250 mg quercetin:250 mg licorice ethanol extract and 500 mg quercetin:500 mg licorice ethanol extract. Formula 2 included dosages of quercetin anhydrate and licorice at 250 mg quercetin:125 mg licorice ethanol extract; 500 mg quercetin:250 mg licorice ethanol extract; and 1000 mg quercetin:500 mg licorice ethanol extract. Formula 3 included dosages of quercetin and licorice at 1000 mg quercetin:200 mg licorice ethanol extract. The study lasted 35 days. Eight separate groups of rats were tested with 15 rats in each group. Two of the eight groups of rats tested were control groups. One was a placebo control group and the other group received 50 μg/kg (10 μg/200 g)/3× per week parathyroid hormone. Parathyroid hormone, known as an anabolic agent, served as a positive control. See, e.g., Turner et al., "Disuse in adult male rats attenuates the bone anabolic response to a therapeutic dose of parathyroid hormone." *J. Appl Physiol.* 2006. Vol. 101:881-886, the entire contents of which are incorporated herein by reference.

Table 7 below indicates the formula given to each of the 8 test groups. The dosages in Table 7 are based on the recommended human daily dosages. FDA dose conversion formula (Human equivalent dose (HED, mg/kg)=rat dose in mg/kg×(rat weight in kg/human weight in kg)$^{0.33}$) was used to convert the human dose to the rat dose.

HED=rat $NOAEL \times (W\text{-rat}/W\text{-human})^{(1-b)}$, $b=0.67$.

In Table 7, Q=quercetin and L=licorice.

TABLE 7

Formulas tested in the In Vivo Study

| Group #: | Formula: | Human Daily Dosage (mg): |
|---|---|---|
| 1 | Q + L (Formula 1) - 1:1 | Q = 250, L = 250 |
| 2 | Q + L (Formula 1) - 1:1 | Q = 500, L = 500 |
| 3 | Q + L (Formula 2) - 2:1 | Q = 250, L = 125 |
| 4 | Q + L (Formula 2) - 2:1 | Q = 500, L = 250 |
| 5 | Q + L (Formula 2) - 2:1 | Q = 1000, L = 500 |
| 6 | Q + L (Formula 3) - 5:1 | Q = 1000, L = 200 |
| 7 | Placebo (null treatment) | |
| 8 | Positive Control (Parathyroid Hormone - 50 μg/kg (10 μg/200 g)/3 × per week) | |

Female, Sprague Dawley rats were used (200-250 gm each, ~12-14 weeks old). Animals were fed at 15 gm/day, which included either a placebo diet or one of the formulas listed above, for a period of 35 days from the beginning of the experiment. Chow was made available each morning to the rats at the rate of 15 grams/rat/day. The rats were allowed free access to water and housed in appropriate cages for the entire experiment. Unrestricted activity was allowed during the entire experiment, which lasted 35 days.

The effectiveness of the formulas on bone formation was assessed by outcome measurements that included biomechanical measurement (to assess bone strength and function information), micro-CT (to analyze virtual bone quality and function information), and histomorphology measurement (to analyze bone quality and functional information). Method of conducting a histomorphological measurement are described by Pa Revell, "Histomorphometry of Bone," *J. Cline. Pathol.*, 1983. Vol. 36:1321-1331, the entire contents of which are incorporated herein by reference. The terminology and units used are those recommended by the Histomorphometry Nomenclature Committee of the American Society for Bone and Mineral Research. Methods of conducting a micro-CT measurement are described at Jiang et al., "Micro CT and Micro MR imagining of 3D architecture of animal skeleton." *J. Musculoskel Neuron Interact* 2000. Vol. 1:45-51, the entire contents of which are incorporated herein by reference. These measurements were determined after 35 days of treatment.

Six animals from each group were sacrificed on day 35 following treatment. Femurs were used for histomorphology analysis. To determine the effect of the different formulas on bone formation, trabecula bone volume, trabecular cells number and trabecular separation were assessed by histomorphology technique. In the below table, Table 8, superscript a ([a]) means that the result is significantly different ($p<0.05$) to the placebo group (null treatment). Difference with $p<0.05$ are considered significant. As shown below in Table 8, the positive control group, PTH, showed a significant increase in bone volume (55.83%), a significant increase in trabecular cells number (19.57%), and a reduction in trabecular separation (38.30%) after treatment with PTH as compared to the placebo group. Similarly, the formula administered to Group 3 demonstrated a significant increase in bone volume (47.59%), a significant increase in trabecular cells number (24.19%), and a reduction in trabecular separation (23.52%) as compared to the placebo group, and its effectiveness was comparable to the PTH treatment.

that more new bone tissues can be formed. The outcome of bone formation rate was consistent with the observed change of bone mineral apposition rate. The formula administered to group 3 showed a significant increase in bone formation rate (51.37%) as compared to the placebo group and its effectiveness was comparable to PTH treatment (45.83%).

Another efficacy determination technique used in this study was micro-CT measurement, which can provide virtual bone quality, structure and functional information. The results of this analysis are reported below in Table 9.

Obtaining information from a wide range of parameters such as bone mineral density (BMD), bone volume (% bone volume/total volume), trabecular number, and trabecular separation is critical for bone structure assessment quantitatively and qualitatively. Among these parameters, the outcome of bone volume, trabecular number, and trabecular separation correlate with bone health.

The results reported in Table 9 indicate that the formulas administered to groups 2 and 5 effectively enhanced osteoblastogenesis and significantly increased bone mineral density (BMD) as compared to the placebo group and their effectiveness was comparable to PTH treatment. Results also indicate that the formulas administered to groups 1, 2, and 5 significantly increased bone volume and the number of

TABLE 8

Histomorphological Measurements

| Group # | % Bone volume | Trabecular number | Trabecular Separation | Trabecular thickness | Bone mineral apposition rate | Bone formation rates |
|---|---|---|---|---|---|---|
| 1 | 3.01% | 7.42% | −8.18% | −6.83% | −0.23% | 4.14% |
| 2 | −6.44% | 2.06% | −8.51% | −11.47% | −2.81% | 15.82% |
| 3 | 47.59%[a] | 24.19%[a] | −23.52% | 13.04% | 26.60%[a] | 51.37%[a] |
| 4 | 11.23% | 4.71% | −7.26% | −6.14% | 9.19% | 16.61% |
| 5 | 29.01%[a] | 4.96% | −9.07% | −8.95% | 3.18% | 20.28% |
| 6 | −6.63% | −8.33% | −7.35% | 5.36% | 9.59% | 3.20% |
| PTH | 55.83%[a] | 19.57%[a] | −38.30% | 7.35% | 28.51%[a] | 45.83%[a] |

Table 8 demonstrates that formulas administered to group 5 demonstrated a significant difference in trabecular bone volume as compared to placebo ($P<0.05$).

In addition, Table 8 reports measurements of trabecular bone thickness. A higher value of bone thickness indicates a greater amount of mineral depositing in the bone, which can result in an increase in bone mass. The formula administered to group 3 significantly increased trabecular bone thickness (13.04%) as compared to the placebo group and its effectiveness was comparable to PTH treatment (7.35%).

Bone mineral apposition rate (MARs), also reported by Table 8, was determined by measuring the mean interlabel distance divided by the time interval (5 days) between the two fluorochromes administered. A greater bone mineral apposition rate (or mineralizing surface) means that there is more new bone deposited. This outcome should correspond to trabecular bone thickness outcome. Indeed, after 35 days of treatment, the formula administered to group 3 showed a significant increase in bone mineral apposition rate (26.60%) as compared to the placebo groups and its effectiveness was comparable to PTH treatment (28.51%).

Table 8 additionally provides values for bone formation rates (BFRs). BFRs were calculated from the extent of bone surface labeled with tetracycline (viewed using epifluorescence) and the distance between the labels in areas where 2 labels are present (calcein and tetracycline) and it was expressed as square micrometer per cubic micrometer per day ($\mu m^2/mm^3/day$). A greater bone formation rate means trabecular cells and reduced trabecular separation as compared to the placebo group and their effectiveness was comparable to PTH treatment. In Table 9, superscript a ([a]) indicates the result is significantly different ($p<0.05$) from the placebo group. Difference with $p<0.05$ are considered significant.

TABLE 9 micro-ct Measurements

| Group # | Bone Mineral Density (BMD) | % Bone Volume/ Total Volume | Trabecular Number (N/6 mm$^2$) | Trabecular separation (mm) |
|---|---|---|---|---|
| 1 | 17% | 32%[a] | 15%[a] | −22%[a] |
| 2 | 71%[a] | 33%[a] | 14%[a] | −22%[a] |
| 3 | 20% | 15% | 7% | −9% |
| 4 | 31% | 13% | 5% | −8% |
| 5 | 74%[a] | 25%[a] | 14%[a] | −19%[a] |
| 6 | 20% | 9% | 4% | −4% |
| PTH | 86%[a] | 32%[a] | 25%[a] | −28%[a] |

Besides bone mass and bone volume evaluation, bone strength was examined mechanically using two different parameters. One parameter measured the maximum force needed to fracture the bone and the other determined the stiffness (the elasticity) of bone. Methods of determining bone strength and stiffness are described by Sturmer et al., "Standardized Bending and Breaking Test for the Normal and Osteoporotic Metaphyseal Tibias of the Rat: Effect of Estradiol, Testosterone, and Raloxifene," *J. Bone and Mineral Research*, 2006. Vol. 21(1):89-96, the entire contents of which are incorporated herein by reference.

In Table 10, results indicate that there were no statistical differences in the maximum force needed to fracture the bone and stiffness of bone between any treatment groups including the positive control group (PTH) and the placebo group. No effect from the positive control group could be due to a relative low dose of PTH employed at only a frequency of 3 times per week. Although PTH is a powerful anabolic agent, the PTH dose was specifically chosen to provide a moderate effect on bone formation without inducing any adverse effect.

TABLE 10

Biomechanical Measurements

| Group # | Maximum Force Required to Fracture Bones | Bone Stiffness |
|---|---|---|
| 1 | −0.1% | −0.1% |
| 2 | −0.1% | 0.0% |
| 3 | 0.0% | 0.0% |
| 4 | 0.0% | 0.0% |
| 5 | −0.1% | −0.1% |
| 6 | 0.0% | 0.0% |
| PTH | 0.0% | 0.0% |

Example 4

Inhibition of RANK-L Study

Weigh between 150 to 250 mg of each ingredient into a 15 ml conical bottomed tube. Dissolve in a solution of 50% DMSO:30% Ethanol:20% water, such as to end with a final stock solution of 50 µg/ml. For solvent control, mix 1.5 ml DMSO, 0.9 ml ethanol, and 0.6 ml water. Vortex thoroughly. Sonicate for 10 minute in water bath, room temperature. Vortex thoroughly again. Dilute ingredient stocks in fresh phenol red-free media.

Human osteosarcoma cell line, MG-63 (ATCC #CRL-1427), is maintained in phenol-red containing MEM (as recommended by ATCC) at 37° C. and 5% $CO_2$. Twenty-four hours prior to experimentation, $3 \times 10^5$ cells are seeded in 12-well plates in phenol-red free MEM. Spent medium is removed from wells and MG-63 cells (ATCC #CRL-1427) are pretreated with 1, 0.1, 0.01 µg/ml of each test ingredient or 30 ng/ml TGF-beta (+control) for 4 hours at 37° C., 5% $CO_2$. Stock solution of TGF-beta is 30 µg/ml (from R&D Systems, cat #100-B-001).

After pretreatment incubation period, 10 µg/ml IL-1b (Calbiochem (catalog #407615) and stock solution at 10 µg/ml, cat #407615) were added to the cell cultures for 18 hours at 37° C. Supernatant media from the treated and stimulated cells were removed and total RANK-L proteins were measured using RANK-L ELISA (in triplicate) as described by manufacturer (from APOTECH, catalog #APO-54N-016-k101). The resulting protein quantity was compared to that of media (null) treated stimulated cells to determine percent decrease in total RANK-L protein.

The above-described assay procedure was used to determine the ability of extracts of: *Ginkgo biloba*, green tea, *Sophora fructus japonica*, *Rehmannia* sp., pomegranate, Siberian ginseng, ipriflavone, grape seed, Dong quai, and *Sophora japonica*, to inhibit RANK-L expression, production, or release. The results of this assay are reported below in Table 11. Decreases of 10% or greater are considered significant.

TABLE 11

Production/Release of RANK-L Protein (relative to untreated control)

| Ingredient (tested at 1 µg/ml): | % Change in Production/Release Levels (compared to untreated control) |
|---|---|
| Ginkgo biloba | 31% decrease |
| Green tea | 19% decrease |
| Sophora Fructus Japonica | 45% decrease |
| Rehmannia sp. | 74% decrease |
| Pomegranate | 20% decrease |
| Pomegranate (Naturex) | 14% decrease |
| Siberian ginseng | 50% decrease |
| Ipriflavone | No effect |
| Grape Seed Extract | 11% decrease |
| Dong Quai (20:1 extraction ratio) | 16% decrease |
| Sophora japonica (NuPharma) | 42% decrease |

Based on the results reported at Table 11, it was determined that pomegranate extract, ipriflavone (Ostivone), grape seed extract (40% proanthocyanidins) and green tea extract (40% EGCG) showed the positive effect on inhibition of RANK-L production/release. Therefore, various combinations of these ingredients were tested, using the RANK-L inhibition assay described above, to determine what level of inhibition of RANK-L production/release could be achieved. The results are reported below in Table 12. As these reports demonstrate, the combination of 10 µg/ml of Pomegranate, 10 µg/ml Ipriflavone, 1 µg/ml Grape Seed extract, and 1 µg/ml Green tea was found to be the formula that maximized the inhibition of RANK-L synthesis in response to IL-1B protein stimulus of osteoblast cells. The results also show that anything with pomegranate generally performed well. Further, no major interference was found among the ingredients.

TABLE 12

RANK-L Inhibition

| Ingredient (dosage): | n | RANK-L inhibition (%) |
|---|---|---|
| Organic Olive Juice Powder (100 µg/ml) | 2 | 41.5 ± 4.0 |
| Organic Olive Juice Powder (10 µg/ml) | 6 | 19.7 ± 2.2 |
| Organic Olive Juice Powder (1 µg/ml) | 6 | No inhibition |
| Organic Olive Juice Powder (0.1 µg/ml) | 3 | No inhibition |
| Pomegranate extract (30 µg/ml) | 2 | 58.6 ± 1.5 |
| Pomegranate extract (20 µg/ml) | 2 | 56.2 ± 2.6 |
| Pomegranate extract (10 µg/ml) | 3 | 48.3 ± 3.1 |
| Pomegranate extract (10 µg/ml) | 2 | 46.9 ± 10.7 |
| Pomegranate extract (10 µg/ml) | 2 | 48.4 ± 1.1 |

TABLE 12-continued

RANK-L Inhibition

| Ingredient (dosage): | n | RANK-L inhibition (%) |
|---|---|---|
| Pomegranate extract (10 μg/ml) | 3 | 49.4 ± 3.3 |
| Pomegranate extract (1 μg/ml) | 3 | 19.3 ± 2.1 |
| Pomegranate extract (0.1 μg/ml) | 3 | 4.7 ± 4.2 |
| Ipriflavone (Ostivone) (10 μg/ml) | 3 | 0 ± 4.3 |
| Ipriflavone (Ostivone) (10 μg/ml) | 3 | 2.8 ± 3.9 |
| Ipriflavone (Ostivone) (10 μg/ml) | 3 | 0 ± 2.5 |
| Ipriflavone (Ostivone) (1 μg/ml) | 2 | 0.8 ± 0.3 |
| Grape Seed Extract (40% OPC) (10 μg/ml) | 3 | 18.7 ± 6.9 |
| Grape Seed Extract (40% OPC) (10 μg/ml) | 2 | 21.9 ± 0.6 |
| Grape Seed Extract (40% OPC) (5 μg/ml) | 3 | 13.1 ± 3.4 |
| Grape Seed Extract (40% OPC) (2 μg/ml) | 2 | 10.3 ± 1.6 |
| Grape Seed Extract (40% OPC) (1 μg/ml) | 3 | 8.0 ± 2.2 |
| Grape Seed Extract (40% OPC) (1 μg/ml) | 2 | 10.7 ± 1.0 |
| Grape Seed Extract (40% OPC) (0.1 μg/ml) | 2 | 0 ± 4.3 |
| Green Tea Extract (40% EGCG) (10 μg/ml) | 3 | 23.9 ± 1.4 |
| Green Tea Extract (40% EGCG) (10 μg/ml) | 3 | 22.6 ± 7.5 |
| Green Tea Extract (40% EGCG) (1 μg/ml) | 3 | 10.2 ± 1.6 |
| Green Tea Extract (40% EGCG) (0.1 μg/ml) | 3 | 0 ± 2.6 |
| Pomegranate + Ipriflavone (Ostivone) (10 μg/ml each) | 2 | 45.7 ± 2.4 |
| Pomegranate + Ipriflavone (Ostivone) (10 μg/ml each) | 2 | 48.0 ± 2.8 |
| Pomegranate + Ipriflavone (Ostivone) (10 μg/ml each) | 3 | 46.9 ± 5.3 |
| Pomegranate (10 μg/ml) + Ipriflavone (Ostivone) (1 μg/ml) | 2 | 48.3 ± 3.5 |
| Pomegranate (10 μg/ml) + Ipriflavone (Ostivone) (0.1 μg/ml) | 2 | 45.6 ± 4.0 |
| Pomegranate (1 μg/ml) + Ipriflavone (Ostivone) (10 μg/ml) | 3 | 21.6 ± 5.2 |
| Pomegranate (10 μg/ml) + Ipriflavone (Ostivone) (10 μg/ml) + Grape Seed Extract (10 μg/ml) | 2 | 63.3 ± 0.7 |
| Pomegranate (10 μg/ml) + Ipriflavone (Ostivone) (10 μg/ml) + Grape Seed Extract (1 μg/ml) | 2 | 64.6 ± 4.9 |
| Pomegranate (10 μg/ml) + Ipriflavone (Ostivone) (10 μg/ml) + Grape Seed Extract (0.1 μg/ml) | 2 | 49.9 ± 2.5 |
| Pomegranate + Ipriflavone (Ostivone) + Grape Seed Extract (10 μg/ml each) | 2 | 42.8 ± 8.9 |
| Pomegranate (10 μg/ml) + Ipriflavone (Ostivone) (10 μg/ml) + Green Tea Extract (10 μg/ml) | 3 | 39.0 ± 2.9 |
| Pomegranate (10 μg/ml) + Ipriflavone (Ostivone) (10 μg/ml) + Green Tea Extract (1 μg/ml) | 2 | 54.6 ± 1.1 |
| Pomegranate (10 μg/ml) + Ipriflavone (Ostivone) (10 μg/ml) + Green Tea Extract (0.1 μg/ml) | 2 | 37.5 ± 8.1 |
| Pomegranate + Ipriflavone (Ostivone) + Green Tea Extract (10 μg/ml each) | 3 | 23.5 ± 2.3 |
| Pomegranate (10 μg/ml) + Ipriflavone (Ostivone) (10 μg/ml) + Grape Seed Extract (10 μg/ml) + Green Tea Extract (10 μg/ml) | 3 | 42.9 ± 1.1 |
| Pomegranate (10 μg/ml) + Ipriflavone (Ostivone) (10 μg/ml) + Grape Seed Extract (10 μg/ml) + Green Tea Extract (0.1 μg/ml) | 2 | 60.8 ± 0.9 |
| Pomegranate (10 μg/ml) + Ipriflavone (Ostivone) (10 μg/ml) + Grape Seed Extract (1 μg/ml) + Green Tea Extract (0.1 μg/ml) | 3 | 55.1 ± 1.8 |
| Pomegranate (10 μg/ml) + Ipriflavone (Ostivone) (10 μg/ml) + Grape Seed Extract (1 μg/ml) + Green Tea Extract (1 μg/ml) | 3 | 68.6 ± 2.6 |
| Pomegranate (10 μg/ml) + Ipriflavone (Ostivone) (10 μg/ml) + Grape Seed Extract (1 μg/ml) + Green Tea Extract (10 μg/ml) | 3 | 65.2 ± 1.1 |
| Pomegranate (10 μg/ml) + Ipriflavone (Ostivone) (10 μg/ml) + Grape Seed Extract (0.1) + Green Tea Extract (1 μg/ml) | 3 | 52.3 ± 0.7 |
| Pomegranate + Ipriflavone (Ostivone) + Grape Seed Extract + Green Tea Extract (10 μg/ml each) | 3 | 38.0 ± 3.5 |
| Ipriflavone (Ostivone) + Grape Seed Extract + Green Tea Extract (10 μg/ml each) | 3 | 9.7 ± 2.8 |
| Pomegranate + Grape Seed Extract + Green Tea Extract (10 μg/ml each) | 3 | 26.9 ± 4.8 |
| Pomegranate (10 μg/ml) + Grape Seed Extract (1 μg/ml) | 2 | 52.7 ± 1.0 |
| Pomegranate (10 μg/ml) + Grape Seed Extract (1 μg/ml) | 2 | 51.1 ± 1.8 |
| Pomegranate (20 μg/ml) + Grape Seed Extract (2 μg/ml) | 2 | 58.2 ± 0.5 |
| Pomegranate (30 μg/ml) + Grape Seed Extract (1 μg/ml) | 2 | 64.3 ± 2.1 |
| Pomegranate (30 μg/ml) + Grape Seed Extract (2 μg/ml) | 2 | 59.9 ± 1.2 |
| Pomegranate (30 μg/ml) + Grape Seed Extract (5 μg/ml) | 2 | 57.2 ± 3.1 |

Example 5

Isolation of Punicalagins from Pomegranate

Fresh pomegranates were peeled to separate the seeds from the peels. The seeds, peels, and fruit flesh were separately extracted using a water and alcohol combination (80:20). Each of the peels, seeds, and flesh yielded extracts with punicalagins but the pomegranate peel extract yielded the highest levels of punicalagins. In addition, water was shown to be the best extraction solvent for extracting puncalagins.

Example 6

Inhibition of RANK-L by Punicalagins

Punicalagin test samples are extracted from pomegranates, including from pomegranate peels, skins, fleshy fruit, and seeds using 100% DMSO at 100 mg/ml. Particulate matter in the extraction is not removed. The punicalagin test samples are diluted in MEM without phenol red (estrogenic) and 0.1% FBS to lower background signaling to ten times the final concentrations. Final DMSO concentrations are kept below 0.2% and are kept constant during treatments. DMSO solvent control is used in the untreated group.

MG63 cells (ATCC #CRL-1472), a human-derived osteosarcoma cell line, are plated at 200,000 cells per well in a 12 well plate with phenol red free MEM at 10% FBS. The next day the media is changed to phenol red free MEM at 0.1% FBS. The cells are incubated for four hours and then treated with punicalagin test samples at concentrations of 1, 10, and 100 µg/ml.

After four hours of treatment, IL-1b (Calbiochem (catalog #407615), stock solution at 10 µg/ml, cat #407615) are added to a final concentration of 3 ng/mL. The treated cells the stimulus, IL-1b, are then allowed to incubate for 16 hours at 37° C.

After 16 hours the cells are lysed and the RNA is extracted from the cells with the RNasy purification kit (Qiagen). RNA is reverse transcribed to cDNA and quantified by qPCR using 2-step qRT-PCR reagents (Invitrogen), and 4 µL of purified RNA. Annealing temperature is 57° C. in the Stratagene Mx4000 with 1 µL of RANK-L gene specific primers in a 50 µL reaction (10 µM initial concentration; HLUX3013920, Invitrogen Inc.).

RANK-L and GAPDH gene expression Ct data are obtained. RNA is quantified with adjustments for GAPDH expression. The untreated control values for RANK-L expression are used to evaluate treatment affects. The results are reported below in Table 13.

TABLE 13

Effect of Punicalagins on RANK-L Expression

| Ingredient | N | RANK-L Expression (fold increase) |
| --- | --- | --- |
| Untreated | 2 | 1.0 ± 0.1 |
| IL1B (3 µg/ml) | 2 | 3.3 ± 0 |
| Punicalagins 1 µg/ml | 2 | 2.6 ± 0.5 |
| Punicalagins 10 µg/ml | 2 | 1.9 ± 0.4 |
| Punicalagins 100 µg/ml | 2 | 0.7 ± .02 |

As shown in Table 13, punicalagins purified from pomegranates inhibit IL-1b stimulated RANK-L gene expression in a dose dependent manner and completely inhibit RANK-L expression at 100 µg/mL.

Example 7

Inhibition of Type IV Collagenase (MMP9) Protein Expression by Punicalagins from Pomegranate Keratinocytes and fibroblasts were co-cultured in DMEM containing 0.5% BSA. Co-cultures were exposed to various concentrations of punicalagins (ranging from 0.1%-10%) were extracted from pomegranates. Specifically, the ability of the pomegranate extracts to inhibit type IV collagenase protein (matrix metalloproteinase-9/MMP9) expression at concentrations of 1.0 µg/ml, 10 µg/ml, and 100 µg/ml were tested. Following exposure to the pomegranate extracts, the co-culture cells were stimulated with 10 ng/ml of IL-1B for 18 hours. Following stimulation with IL-1B for 18 hours, and MMP9 concentration was determined in the media as shown below in Table 14.

TABLE 14

Effect of Pomegranate Extracts on MMP9 (type IV collagenase) protein expression

| Tested Pomegranate Extract | N | Inhibition of MMP9 |
| --- | --- | --- |
| Untreated | 2 | 1.0 ± 0.1 |
| IL1B (10 ng/ml) | 2 | 1.65 |
| Punicalagins 1 µg/ml | 4 | 1.5 ± .06 |
| Punicalagins 10 µg/ml | 4 | 1.2 ± .04 |
| Punicalagins 100 µg/ml | 4 | 1.0 ± 0.1 |

The results reported at Table 14 demonstrate that punicalagins from pomegranate inhibit IL-1B stimulated collagenase release (MMP9) from keratinocytes in vitro. These results demonstrate that punicalagins inhibit inflammation-stimulated breakdown of the extracellular matrix. Activated osteoclasts reduce bone strength and increase bone loss by secreting matrix digesting enzymes (MMPs) to break down the bone's collagen/calcium phosphate framework. Blocking the destruction of bone's collagen/calcium framework will be expected to maintain/improve bone strength and bone structure. Increased bone strength and bone structure are characterized by increased bone mineral density, increased bone volume, increased trabecular cell number, decreased trabecular separation, improved bone architecture, increase in maximum force needed to fracture bone, and increase in stiffness of bone.

Example 8

Inhibition of C. histolyticum Collagenase Activity by Grape Seed and Pomegranate Extracts Samples are prepared by weighing out 100 mg of powder. A 50 mg/ml total extract of the sample is then prepared by sequential addition of DMSO:Ethanol:water in a ratio of 5:3:2. Therefore for 100 mg of powder, 1 ml DMSO, 0.6 ml ethanol, and 0.4 ml water would be used. The solutions are extensively mixed by vortexing and are then incubated for 10 min in a sonic water bath. The samples are diluted from the stock concentration of 50 mg/ml to test concentrations.

Inhibition of collagenase activity is assayed using a commercially available kit (Molecular Probes, Eugene, Oreg.). The kit is based on an ability to digest a collagen substrate labeled with a fluorescent tag. Prior to digestion, the fluorescence of the substrate is quenched. After exposure to collagenase, the substrate is cleaved abolishing the quenching effect so that the fluorescence increases. The samples (prepared according to above procedure) are first added to the collagenase (0.2 Units/ml) provided with the kits. The fluorescent substrate (50 µg/ml) is then added and the reaction is incubated for an hour at ambient temperature. Fluorescence is read on a plate reader at excitation/emission of 495/515 nm. Data are expressed as % control compared to MMP without any inhibitor added. A decrease from 100% total enzyme activity is considered a positive response.

A dose dependent response towards reduction of collagenase activity was observed for both the pomegranate extract and the grape seed extract (Table 15).

Activated osteoclasts reduce bone strength and increase bone loss by secreting matrix digesting enzymes (MMP's) to break down the bone's collagen/calcium phosphate framework. By the mechanism suggested here, the grape seed and pomegranate extracts in particular are found to be potent inhibitors of collagenase activity. By this activity a net positive balance of collagen production may be achieved resulting in the maintenance or improvement of bone strength and bone integrity.

TABLE 15

Inhibition of *C. histolyticum* collagenase activity by Grape Seed and Pomegranate Extracts

| Sample | Concentration (µg/ml) | % Collagenase Activity |
|---|---|---|
| Pomegranate extract | 1 | 96.7 ± 10.0% |
|  | 10 | 86.3 ± 5.9% |
|  | 100 | 29.2 ± 5.7% |
| Grape seed extract | 1 | 98.9 ± 3.0% |
|  | 10 | 48.8 ± 2.3% |
|  | 100 | −7.2 ± 4.3% |
| Collagenase only | 0 | 100.0 ± 0.8% |

Example 9

Calvarial Assay to Measure Inhibition of Bone Resorption

In order to label cells of newborn mice in utero, pregnant CD-1 female mice (at timed day 15) were injected with $^{45}$Ca (25 uCi/mouse). The calvaria (skull bones) from the 4 day old pups were dissected out and cut in half. The excised half calvaria were placed on metal grids (at the surface) in 1 ml of BGJ growth medium (Sigma) containing 0.1% BSA with glutamine and Pen/Strep added. The bones were incubated at 37° C. in a 5% $CO_2$ humidified incubator for a period of 24 hours following which they were transferred to wells containing 1 ml media with factors added (IL-1, PTH and or compounds.) The treated bones were incubated under the above conditions for a further 72 hours. After this incubation period the bones were removed and placed into 20% TCA in a scintillation vial for 1.5 hours (to measure labeled calcium retained in the bone) and then counted with scintillation fluid. In addition, 0.4 ml of the media was also counted (to determine the amount of labeled calcium released from the bones). The results were expressed as % $^{45}$Ca release and can be further reported as T/C ratios.

For some factors and compounds, modification of this procedure can be used. As most of the osteoclasts are formed in the calvaria following the preincubation period, the factors that affect osteoclast formation may have a greater effect during the preincubation period. Thus, for a number of the compounds, they were included in the preincubation media.

The extracts tested in this assay include *Ginkgo biloba* extract, green tea extract, *Sophora fructus japonica* extract, *Rehmannia* sp. extract, pomegranate extract, Siberian ginseng, ipriflavone, grape seed extract, and Dong quai extract. The results of testing these extracts in the calvarial assay are reported below in Table 16.

In Table 16, R-1=*Rehmannia* sp. (EUL), SFJ=*Sophora Fructus Japonica*, SG=Siberian Ginseng, SJ=*Sophora Japonica* (NuPharma), I=Ipriflavone, GB=*Ginkgo Biloba*, GT=Green Tea, P-1=Pomegranate extract, P-2=Pomegranate extract (Naturex), GS=Grape Seed, DQ=Dong Quai extract. In the below table, superscript a ($^a$) means that the result is significantly different (p<0.05) to the blank sample (concentration at 0 µg/ml) result. Differences with p≤0.05 (i.e. where the margin of error is less than or equal to 5%) were considered significant. As shown in table 16, pomegranates, ipriflavone, green tea extract, and grape seed extract inhibited IL-1b induced bone resorption/release of calcium.

TABLE 16

Calvarial Data - Inhibition of Bone Resorption/Release of $Ca^{2+}$

| Conc. IL-1 + µg/ml | R-1 | SFJ | SG | SJ | I | GB |
|---|---|---|---|---|---|---|
|  |  |  | % Release |  |  |  |
| IL-1 + 100 µ/ml | 35.50 ± 2.18 | 30.50 ± 1.85 | 38.25 ± 1.93 | 34.50 ± 2.78 | 19.25 ± 1.03$^a$ | 33.50 ± 2.78 |
| IL-1 + 10 µg/ml | 25.70 ± 1.49 | 29.00 ± 2.74 | 41.25 ± 1.11 | 31.70 ± 1.11 | 32.50 ± 3.30 | 34.50 ± 3.52 |
| IL-1 + 1 µg/ml | 31.50 ± 0.96 | 28.25 ± 2.25 | 39.25 ± 1.38 | 33.00 ± 3.42 | 38.00 ± 1.41 | 37.50 ± 1.44 |
| IL-1 | 28.70 ± 2.56 | 28.70 ± 2.56 | 45.70 ± 1.65 | 32.50 ± 3.18 | 40.00 ± 2.12 | 31.50 ± 2.10 |
| No IL-1 | 9.50 ± 0.65 | 9.50 ± 0.65 | 14.75 ± 2.40 | 10.50 ± 0.65 | 10.50 ± 0.85 | 11.25 ± 1.32 |

| Conc. IL-1 + µg/ml | GT | P-1 | P-2 | GS | DQ |
|---|---|---|---|---|---|
|  |  |  | % Release |  |  |
| IL-1 + 100 µ/ml | 11.00 ± 0.71$^a$ | 12.00 ± 1.41$^a$ | 8.75 ± 0.25$^a$ | 13.75 ± 1.41$^a$ | 38.50 ± 1.32 |
| IL-1 + 10 µg/ml | 36.00 ± 2.04 | 25.50 ± 1.71$^a$ | 25.25 ± 2.36$^a$ | 42.75 ± 1.71 | 37.25 ± 2.14 |
| IL-1 + 1 µg/ml | 40.25 ± 2.29 | 39.00 ± 2.97 | 36.50 ± 1.85$^a$ | 37.75 ± 2.97 | 40.50 ± 1.55 |
| IL-1 | 31.50 ± 2.10 | 38.25 ± 0.25 | 45.70 ± 1.65 | 40.00 ± 0.25 | 38.25 ± 0.25 |
| No IL-1 | 11.20 ± 1.32 | 15.75 ± 1.80 | 14.70 ± 2.43 | 10.25 ± 1.80 | 15.75 ± 1.70 |

The calvarial assay described above was repeated with various combinations of the extracts useful in compositions of the present invention. The results for each formulation are reported below in Table 16.

In Table 17, P=Pomegranate, I=Ipriflavone, GS=Grape Seed, GT=Green Tea. Alendronate was used as a positive control. In the below table, superscript a ($^a$) means that the result is significantly different (p<0.05) to the blank sample (concentration at 0 µg/ml) result. Differences with p≤0.05 (i.e. where the margin of error is less than or equal to 5%) were considered significant. As shown in Table 17, all tested combinations inhibited IL-1b induced bone resorption/release of calcium.

TABLE 17

Calvarial Data - Inhibition of Bone Resorption/Release of Calcium By Combinations of Extracts

| Conc. μ/ml | Alendronate % Release | Conc. μg/ml | P:GS:I 500:50:600 | P:GS 1000:100 | P:GT 1000:100 | P:GS:GT 1000:100:100 | P:I:GT 500:600:50 | I 600 |
|---|---|---|---|---|---|---|---|---|
| | | | | | % Release | | | |
| IL-1 + 100 μM | 12.00 ± 0.17$^a$ | IL-1 + 100 μg/ml | 9.00 ± 0.50$^a$ | 9.00 ± 0.41$^a$ | 9.75 ± 0.48$^a$ | 9.00 ± 0.41$^a$ | 9.50 ± 0.29$^a$ | 17.50 ± 1.66$^a$ |
| IL-1 + 10 μM | 14.07 ± 1.05$^a$ | IL-1 + 10 μg/ml | 26.00 ± 2.06$^a$ | 22.25 ± 1.44$^a$ | 22.25 ± 2.14$^a$ | 21.25 ± 1.80$^a$ | 23.50 ± 2.06$^a$ | 30.25 ± 4.03 |
| IL-1 + 1 μM | 17.00 ± 1.15$^a$ | IL-1 + 1 μg/ml | 40.75 ± 4.48 | 34.0 ± 3.70 | 36.25 ± 4.94 | 32.75 ± 3.82 | 44.50 ± 0.96 | 29.75 ± 4.54 |
| IL-1 + 0.1 μM | 28.50 ± 1.19 | IL-1 | 35.50 ± 3.01 | 35.50 ± 3.01 | 30.25 ± 1.97 | 30.25 ± 1.97 | 36.255 ± 2.18 | 36.25 ± 2.18 |
| IL-1 | 30.00 ± 0.99 | No IL-1 | 10.50 ± 0.65 | 10.50 ± 0.65 | 11.25 ± 0.75 | 11.25 ± 0.75 | 13.00 ± 1.08 | 13.00 ± 1.08 |
| No IL-1 | 10.00 ± 0.78 | | | | | | | |

Example 10

In Vivo Study to Measure Inhibition of RANK-L and Inhibition of Bone Resorption Two different formulas were tested in an in vivo study involving female, intact rats, aged approximately 12-14 weeks, with approximate body weights between 200-250 grams. Formula 1 included varying dosages of ipriflavone, pomegranate extract, and grape seed extract as reported in Table 18. Formula 2 included varying dosages of pomegranate extract and grape seed extract and a fixed dosage of ipriflavone as reported in Table 18. Three dosages were tested for each formula. The study utilized 8 groups of rats, with 15 rats in each group and lasted approximately 35 days.

Table 18 below indicates the formula given to each of the 8 test groups. The dosages in Table 18 are based on the recommended human dosages and were converted to the appropriate corresponding rat dose using the FDA conversion formula: Human equivalent dose (HED, mg/kg)=rat dose in mg/kg×(rat weight in kg/human weight in kg)$^{0.33}$ HED=rat NOAEL×(W-rat/W-human)$^{(1-b)}$, b=0.67.

In Table 18, I=ipriflavone, P=pomegranate extract, and GS=grape seed extract.

TABLE 18

Dosages and Formulas For Analysis In Vivo

| Group #: | Formula: | Dosage (mg): |
|---|---|---|
| 1 | P + GS | P = 500, GS = 50 |
| 2 | P + GS | P = 1250, GS = 125 |
| 3 | P + GS | P = 2000, GS = 200 |
| 4 | P + GS + I | P = 0, GS = 0, I = 600, |
| 5 | P + GS + I | P = 500, GS = 50, I = 600, |
| 6 | P + GS + I | P = 1250, GS = 125, I = 600, |
| 7 | Placebo | |
| 8 | Positive Control (Alendronate - 0.5 mg/day) | |

To introduce rapid bone resorption caused by estrogen withdrawal, the ovariectomized (OVX) rat model was used in this study. See, e.g. Alam et al., "Effects of Safflower Seed Oil in Osteoporosis-induced Ovariectomized Rats," *Am. J. Chinese Medicine,* 2006. Vol. 34(4): 601-612, the contents of which are incorporated herein by reference. It was important to evaluate the effect of bone resorption caused by the ovariectomy procedure so a Sham control (n=6), a group of female rats without undergoing the ovariectomy procedure, was also included in the study.

This study employed a randomized placebo controlled dose response design. A total of 120 ovariectomized rats (n=15 per group) aged ~12-14 weeks, with body weights of approximately 200-250 grams were randomly assigned to groups for 35 days. Animals were fed at 15 grams/day, which included either a placebo diet or one of the formulas listed above, for a period of 35 days from the beginning of the experiment. Chow was made available each morning to the rats at the rate of 15 grams/rat/day. The rats were allowed free access to water and housed in appropriate cages for the entire experiment. Unrestricted activity was allowed during the entire experiment.

The effectiveness of the formulas on antiresorption was assessed by outcome measurements that included DEXA scan (to determine bone mineral density), biomechanical measurement (to gather bone strength and functional information), micro-CT measurement (to assess virtual bone quality and functional information), and histomorphology measurement (to assess bone quality and functional information). Methods of conducting a histomorphological measurement are described by Pa Revell, "Histomorphometry of Bone," *J. Clin. Pathol.,* 1983. Vol. 36: 1321-1331, the entire contents of which are incorporated herein by reference. The terminology and units used are those recommended by the Histomorphometry Nomenclature Committee of the American Society for Bone and Mineral Research. Methods of conducting a micro-CT measurement are described at Jiang et al., "Micro CT and Micro MR imagining of 3D architecture of animal skeleton." *J. Musculoskel Neuron Interact.* 2000. Vol. 1:45-51, the entire contents of which are incorporated herein by reference. These measurements were determined after 35 days of treatment.

Both DEXA scan and micro-CT measurement results indicated substantial loss of bone mineral density in ovariectomized (OVX) rats compared to sham controlled (non ovariectomized) rats. Bone strength was also significantly reduced as indicated by maximum force to fracture bones and bone stiffness measurements, as well as % bone volume/total volume and trabecular cell number in OVX rats. In addition, a marked increase in the trabecular separation (an average of how far the trabecular are away from each other) was also observed in OVX rats. The positive control group, ALD, was treated with alendronate drug, an effective antiresorption agent known to reduce osteoclastogenesis. See, e.g., Iwamoto et al., "Comparative effects of alendronate and alfacalcidol on cancellous and cortical bone mass and bone mechanical properties in ovariectomized rats." *Exp. Anim.* 2006. vol. 55(4):357-67, the entire contents of which are incorporated herein by reference. The positive control group (ALD) experienced increases in bone mineral density, % bone volume/total volume, and trabecular number and experienced a marked reduction in trabecular separation.

One of the efficacy determination techniques used in this study was micro-CT measurement, which provides virtual bone quality, structure and functional information. As shown below in Table 19, after 35 days of treatment, the formulas administered to groups 2, 3, 4, 5, and 6 were more efficacious than placebo (null treatment) in preventing bone resorption. The outcome of bone mineral density (BMD), bone volume, trabecular cell number and trabecular separation correlates with bone health. Superscript a ($^a$) means the result significantly different from the placebo group. Differences of p<0.05 are considered significant.

TABLE 19

Histomorphological Measurements

| Group # | Bone Mineral Density | % Bone Volume/ Total Volume | Trabecular Number (N/6 mm$^3$) | Trabecular Separation |
|---|---|---|---|---|
| 1 | 21% | 107%$^a$ | 58%$^a$ | −47%$^a$ |
| 2 | 32%$^a$ | 132%$^a$ | 99%$^a$ | −52%$^a$ |
| 3 | 32%$^a$ | 145%$^a$ | 122%$^a$ | −64%$^a$ |
| 4 | 25%$^a$ | 137%$^a$ | 117%$^a$ | −58%$^a$ |
| 5 | 22% | 156% | 96% | −42% |
| 6 | 1% | 11% | 14% | −18% |
| ALD | 124%$^a$ | 632%$^a$ | 313%$^a$ | −88%$^a$ |
| Sham | 41%$^a$ | 374%$^a$ | 281%$^a$ | −82%$^a$ |

In Table 20, results from the bone mineral density indicated that the formulas administered to groups 2, 3, and 4 effectively reduced osteoclastogenesis and increased bone mineral density. Results also indicated that the formulas administered to groups 1, 2, 3, and 4 effectively reduced osteoclastogenesis, increased bone volume increased the number of trabecular cells and reduced trabecular cell separation. Superscript a ($^a$) means the result significantly different from the placebo group. Differences of p<0.05 are considered significant.

TABLE 20

DEXA Measurements

| Group # | Bone Mineral Density |
|---|---|
| 1 | 0% |
| 2 | 7%$^a$ |
| 3 | 10%$^a$ |
| 4 | 5%$^a$ |
| 5 | 5%$^a$ |
| 6 | 3%$^a$ |
| ALD | 35%$^a$ |
| Sham | 14%$^a$ |

Histomorphology measurement was also used as a tool to determine the efficacy of formulas 1 and 2 where trabecular bone volume from each group was quantified. The results from this analysis are reported in Table 21. Superscript a ($^a$) indicates that the result is significantly different from the placebo group. Differences with p<0.05 are considered significant.

As shown in Table 21, formula 1 caused a significant increase in trabecular bone volume (61.4%) compared to the placebo group. The increase in trabecular bone volume while observed, the magnitude was smaller in groups 2 (13.5%) and 3 (13.1%).

TABLE 21

Histomorphological Measurements

| Group # | % Bone Volume |
|---|---|
| 1 | 61.4%$^a$ |
| 2 | 13.5% |
| 3 | 13.1%$^a$ |
| 4 | −12.9% |
| 5 | 6.4% |
| 6 | 41.7% |
| ALD | 214.1%$^a$ |
| Sham | 127.9%$^a$ |

Besides bone mass and bone volume evaluation, bone strength was examined mechanically by two different parameters. One test was conducted to determine the maximum force needed to fracture the bone and the other was to determine the stiffness (the elasticity) of bone. Methods of determining bone strength and stiffness are described by Sturmer et al., "Standardized Bending and Breaking Test for the Normal and Osteoporotic Metaphyseal Tibias of the Rat: Effect of Estradiol, Testosterone, and Raloxifene," *J. Bone and Mineral Research,* 2006. Vol. 21(1):89-96, the entire contents of which are incorporated herein by reference. The results of this analysis are reported below in Table 22. Superscript a ($^a$) means the result significantly different from the placebo group. Differences with p<0.05 are considered significant.

Results listed in table 22 indicate that formula 1 as administered to groups 2 and 3 resulted in an 8.3% and 8.1% increase in maximum force required to fracture bones as compared to the placebo group. Formula 1 as administered to group 3 resulted in a 16.0% increase in bone stiffness relative to the placebo treatment.

TABLE 22

Biomechanical Measurements

| Group # | Maximum Force Required to Fracture Bones | Bone Stiffness |
|---|---|---|
| 1 | −0.4 | 4.9 |
| 2 | 8.3$^a$ | 0.6 |
| 3 | 8.1$^a$ | 16.0$^a$ |
| 4 | −0.6 | 4.6 |
| 5 | 0.9 | 10.2 |
| 6 | 3.0 | 3.3 |
| ALD | −0.4 | 0.2 |
| Sham | −0.3 | 6.0 |

Results from the DEXA scan, biomechanical measurement, micro-CT measurement, and histomorphology measurement clearly illustrated that Formula 1, comprised of pomegranate and grape seed extract, exhibited an ability to improve bone structure and architecture and increase bone strength during estrogen withdrawal.

It is intended that the foregoing detailed description be regarded as illustrative rather than limiting, and that it be understood that it is the following claims, including all equivalents, that are intended to define the spirit and scope of this invention.

The invention claimed is:

1. A method of inhibiting bone resorption in a subject comprising administering a combination of from about 500 mg to about 1500 mg of an extract of pomegranate and from about 35 mg to about 200 mg of an extract of grape seed to the subject wherein the pomegranate and grape seed are each present in defined amounts to provide a ratio of pomegranate to grape seed of about 10:1.

2. The method of claim 1, wherein the administration of the combination results in one or more of the following: increases bone hardness, increases bone strength, improves bone architecture, and increases trabecular bone volume.

3. A method of inhibiting bone resorption in a subject comprising administering the combination of claim 1 to the subject, wherein the combination inhibits, prevents or decreases the release or expression of RANK-L.

4. The method of claim 1, wherein the combination further comprises ipriflavone.

5. The method of claim 1, wherein the combination comprises approximately 1250 mg of an extract of pomegranate and approximately 125 mg of an extract of grape seed.

6. The method of claim 1, wherein the pomegranate extract comprises at least one punicalagin.

7. The method of claim 4 wherein the ipriflavone is present in an amount from about 400-700 mg.

8. The method of claim 7 wherein the ratio of pomegranate:grape seed:ipriflavone:grape seed extract is about 10:12:1.

9. The method of claim 4 wherein the combination further comprises from about 300 to about 700 mg. of green tea.

10. The method of claim 9 wherein the pomegranate, grape seed, ipriflavone, and green tea are each present in defined amounts to provide a ratio of pomegranate:ipriflavone:grape seed extract:green tea of about 10:10:1:1.

* * * * *